US005990092A

United States Patent [19]
Walsh

[11] Patent Number: 5,990,092
[45] Date of Patent: Nov. 23, 1999

[54] GATA-6 TRANSCRIPTION FACTOR: COMPOSITIONS AND METHODS

[75] Inventor: Kenneth Walsh, Carlisle, Mass.

[73] Assignee: St. Elizabeth's Medical Center, Boston, Mass.

[21] Appl. No.: 08/927,394

[22] Filed: Aug. 27, 1997

Related U.S. Application Data

[60] Provisional application No. 60/025,574, Sep. 6, 1996.

[51] Int. Cl.⁶ .......................... A61K 48/00; C12N 15/12; C12N 15/85
[52] U.S. Cl. ..................... 514/44; 435/320.1; 536/23.5
[58] Field of Search ................................ 435/320.1, 375, 435/377; 514/44; 536/23.5

[56] References Cited

U.S. PATENT DOCUMENTS

| | | | |
|---|---|---|---|
| 5,444,157 | 8/1995 | Suzuki et al. | 530/395 |
| 5,502,176 | 3/1996 | Tenen et al. | 536/24.1 |
| 5,503,833 | 4/1996 | Redmond et al. | 424/196.11 |

FOREIGN PATENT DOCUMENTS

WO 95/23161   8/1995   WIPO .

OTHER PUBLICATIONS

Banai et al., "Rabbit Ear Model of Injury–Induced Arterial Smooth Muscle Cell Proliferation," Circulation Research 1991;69:748–756.
Flugelman et al., "Low Level in Vivo Gene Transfer into the Arterial Wall Through a Perforated Balloon Catheter," Circulation 1992;85:1110–1117.
Gregory Gregoriadis, "Liposomes for Drugs and Vaccines," Trends in Biotechnology, vol. 3, No. 9, 1985, pp. 235–241.
Grepin et al., "Induction of Cardiogenesis in Embryonic Stem Cells Following Forced Expression of Transcription Factor Gata–4," Minisymposium 23: Tissue–Specific Gene Expression (1996–2001)—Wednesday, p. 1998.
Grepin et al., "Inhibition of Transcription Factor GATA–4 Expression Blocks in Vito Cardiac Muscle Differentiation," Molecular and Cellular Biology. Aug. 1995, pp. 4095–4102.
Hehrlein et al., "Low–Dose Radioactive Endovascular Stents Prevent Smooth Muscle Cell Proliferation and Neointimal Hyperplasia in Rabbits," Circulation 1995;92:1570–1575.
Jahroudi et al., "Endothelial–Cell–Specific Regulation of von Willebrand Factor Gene Expression," Molecular and Cellular Biology, Feb. 1994, p. 999–1008.
Jiang et al., "Regulation of Cardiac Gene Expression by GATA–4/5/6 Transcription Factors," Abstracts of the 68th Scientific Sessions, p. 3650.
Johnson et al., "Proliferating Cell Nuclear Antigen (PCNA) Is Expressed in activated Rat Skeletal Muscle Satellite Cells," Journal of Cellular Physiology 154:39–43 (1993).
Joulin et al., "A New Approach To Isolate Genomic Control Regions Application to the GATA Transcription Factor Family," Eur. J. Biochem. 232, 620–626 (1995).

Kamensaki et al., "TPA–Induced Arrest of Erythroid Differentiation Is Coupled with Downregulation of Gata–1 and Upreguation of GATA–2 in an Erythroid Cell Line SAM–1," Blood, vol. 87, No. 3 Feb. 1, 1996, pp. 999–1005.
Lee et al., "Cloning of the GATA–Binding Protein that Regulates Endothelin–1 Gene Expression in Endothelial Cells," The Journal of Biological Chemistry, vol. 266, No. 24, Aug. 25, 1991, pp. 16188–16192.
Merika et al., "DNA–Binding Specificity of GATA Family Transcription Factors," Molecular and Cellular Biology, vol. 13, No. 7, Jul. 1993, pp. 3999–4010.
More et al., "A Time Sequence of Vessel Wall Changes in an Experimental Model of Angioplasty," Journal of Pathology, vol. 172, pp. 287–292 (1994).
Nabel et al., "Site–Specific Gene Expression in Vivo by Direct Gene Transfer into the Arterial Wall," Science, vol. 249, Sep. 14, 1990, pp. 1285–1288.
Nemer et al., "Expression and Regulation of a Family of GATA Transcription Factors in the Mammalian Heart," Wednesday, Muscle Gene Expression p. 2434.
Pandolfi et al., "Targeted Disruption of the GATA3 Gene Causes Severe Abnormalities in the Nervous System and in Fetal Liver Haematopoiesis," Nature Genetics, vol. 11, Sep. 1995, pp. 40–44.
Rome et al., "Anatomic Barriers Influence the Distribution of In Vivo Gene Transfer into the Arterial Wall," Arterioscler Thromb. 1994: 14:148–161.
Thuerauf et al., "Regulation of Rat Brain Natriuretic Peptide Transcription: A Potential Role for GATA–Related Transcription Factors in Myocardial Cell Gene Expression," The Journal of Biological Chemistry, vol. 269, Jul. 8, 1994, pp. 17772–17775.
Eric J. Topol. "Caveats About Elective Coronary Stenting," NE J. Med., vol. 331, No. 8, 1994, pp. 539–541.
Yamagata et al., "Of the GATA–Binding Proteins, Only GATA–4 Selectively Regulates the Human Interleukin–5 Gene Promoter in Interleukin–5–Producing Cells Which Express Multiple GATA–Binding Proteins," Molecular and Cellular Biology, vol. 15, No. 7, Jul. 1995, pp. 3830–3839.
Abstract Only Of Alexander et al., "Circulating Human Factor IX Produced in Keratin–Promoter Transgenic Mice: A Feasibility Study for Gene Therapy of Haemophilia B," Hum. Mol. Genet, 1995, Jun: 4(6):993–999.

(List continued on next page.)

*Primary Examiner*—Nancy Degen
*Assistant Examiner*—Robert Schwartzman
*Attorney, Agent, or Firm*—Wolf, Greenfield & Sacks P.C.

[57] ABSTRACT

Methods and compositions for reducing or preventing the proliferation of vascular smooth muscle cells are provided. The method involves the step of administering an isolated GATA-6 molecule to a subject to prevent or reduce vascular smooth muscle cell proliferation. The isolated GATA-6 molecule can be a GATA-6 nucleic acid or a GATA-6 protein.

21 Claims, No Drawings

OTHER PUBLICATIONS

Abstract Only Of Auge et al., "Proliferative and Cytotoxic Effects of Mildly Oxidized Low–Density Lipoproteins on Vascular Smooth–Muscle Cells," Biochem J. 309 (Pt 3):1015 20 (1995).

Abstract Only Of Bai et al., "Neointima formation After Vascular Stent Implantation. Spatial and Chronological Distribution of Smooth Muscle Cell Proliferation and Phenotypic Modulation," Arterioscler Thromb 14:1846–1853 (1994).

Abstract Only Of Brauker et al., "Sustained Expression of High Levels of Human Factor IX from Human Cells Implanted Within an Immunoisolation Device into Athymic Rodents," Hum. Gene Ther. 1998 Apr. 10; 9(6):879–888.

Abstract Only Of Carter et al., "Morphologic Characteristics of Lesion Formation and Time Course of Smooth Proliferative Restenosis Model," J. Am. Coll. Cardiol. 24:1398–405 (1994).

Abstract Only Of Chang et al., "Adenovirus–Mediated Over–Expression of hte Cyclin/Cyclin–Dependent Kinase Inhibitor, p21 Inhibits Vascular Smooth Muscle Cell Proliferation and Neointima Formation in the Rat Carotoid Artery Model of Balloon Angioplasty," J. Clin. Invest 96:2260–8 (1995).

Abstract Only Of Chang et al., "Inhibition of Hypercholesterolemia–Induced Atherosclerosis in the Nonhuman Primate by Probucol. II. Cellular Composition and Proliferation," Arteriscler. Thromb. Vasc. Biol. 15:1631–40 (1995).

Abstract Only Of Conte et al., "Efficient Repopulation of Denuded Rabbit Arteries with Autologous Genetically Modified Endothelial Cells," Circulation 89:2161–9 (1994).

Abstract Only Of Epstein et al., "The Basis of Molecular Strategies for Treating Coronary Restenosis After Angioplasty," J. Am. Coll. Cardiol. 23:1278–88 (1994).

Abstract Only Of Herrmann, et al., "Inhibition of Smooth Muscle Cell Proliferation and Experimental Angioplasty Restenosis by Beta–Cyclodextrin Tetradecasulfate," Arterioscler Thromb. 13:924–31 (1993).

Abstract Only of Hysmith et al., "Comparative Toxicity of the Cardiovascular Toxin Allylamine to Porcine Aortic Smooth Muscle and Endothelial Cells," Toxicology 38:141–50 (1986).

Abstract Only Of Katayose et al., "Consequences of p53 Gene Expression by Adenovirus Vector on Cell Cycle Arrest and Apoptosis in Human Aortic Vascular Smooth Muscle Cells," Biochem. Biophys. Res. Commun. 215:446–51 (1995).

Abstract Only Of Kaushal et al., "Activation of the Myogenic Lineage by MEF2A, a Factor that Induces and Cooperates with MyoD," Science 266:1236–40 (1994).

Abstract Only OfKurki et al., "Monoclonal Antibodies to Proliferating Cell Nuclear Antigen (PCNA)/Cyclin as Probes for Proliferating Cells by Immunofluorescence Microscopy and Flow Cytometry," J. Immunol. Methods 109:49–59 (1988).

Abstract Only OfLafont et al., "Effect of Alpha–Tocopherol on Restenosis After Angioplsaty in a Model of Experimental Atherosclerosis," J. Clin. Invest. 95:1018–25 (1995).

Abstract Only Of Lohr et al., "Comparison of Proliferating Cell Nuclear Antigen (PCNA) Staining and BrdUrd–Labelling Index under Different Proliferative Conditions in Vitro by Flow Cytometry," Cell. Prolif. 28:93–104 (1995).

Abstract Only Of Marino et al., "Proliferating Cell Nuclear Antigen in Developing and Adult Rat Cardiac Muscle Cells," Circ. Res. 69:1353–60 (1991).

Abstract Only Of Mooradian et al., "Nitric Oxide (NO) Donor Molecules: Effect of NO Release Rate on Vascular Smooth Muscle Cell Proliferation in Vitro," J. Cardiovasc. Pharmacol. 25:674–8 (1995).

Abstract Only Of Morishita et al., "A Gene Therapy Strategy Using a Transcription Factor Decoy of the E2F Binding Site Inhibits Smooth Muscle Proliferation in Vivo," Proc. Natl. Acad. Sci. USA 92:5855–9 (1995).

Abstract Only Of Oguchi et al., Vascular Smooth Muscle Cells from Genetically Hyperlipidemic Rabbit (WHHL Rabbit) Exhibit Decreased Growth Response, Atherosclerosis 90:101–8 (1991).

Abstract Only Of Petersen et al., "Sustained Production of Human Transferrin by Transduced Fibroblasts Implanted into Athymic Mice: A Model for Somatic Gene Therapy," J. Invest. Dermtol. 1995 Feb; 104(2):171–176.

Abstract Only Of Pickering et al., "Prevention of Smooth Muscle Cell Outgrowth from Human Atherosclerotic Plaque by a Recombinant Cytotoxin Specific for the Epidermal Growth Factor Receptor," J. Clin. Invest. 91:724–9 (1993).

Abstract Only OfPorreca et al., "Antiproliferative Effect of Desferrioxamine on Vascular Smooth Muscle Cells In Vitro and In Vivo," Arterioscler. Thromb. 14:299–304 (1994).

Abstract Only Of Raja–Walia et al., "Enhancement of Liposome–Mediated Gene Transfer into Vascular Tissue by Replication Deficient Adenovirus," Gene Ther. 2:521–30 (1995).

Abstract Only OfRekhter et al., "Active Proliferation of Different Cell Types, Including Lymphocytes, in Human Atherosclerotic Plaques," Am. J. Pathol. 147:668–77 (1995).

Abstract Only Of Shi et et al., "Transcatheter Delivery of C–MYC Antisense Oligomers Reduces Neointimal Formation in a Porcine Model of Coronary Artery Ballon Injury," Circulation 90:944–51 (1994).

Abstract Only OfSpeir et al., "Inhibition of Smooth Muscle Cell Proliferation by an Antisense Oligodeoxynucleotide Targeting the Messenger RNA Encoding Proliferating Cell Nuclear Antigen," Circulation 86:538–47 (1992).

Abstract Only Of Takeshita et al., "Increased Gene Expression After Liposome–Mediated Arterial Gene Transfer Associated with Intimal Smooth Muscle Cell Proliferation. In Vitro and In Vivo Findings in a Rabbit Model of Vascular Injury," J. Clin. Invest. 93:652–61 (1994).

Abstract Only OfZeymer et al., "Proliferating Cell Nuclear Antigen Immunohistochemistry in Rat Aorta After Balloon Denudation. Comparison with Thymidine and Bromodeoxyuridine Labeling," Am. J. Pathol. 141:685–90 (1992).

Abstract Only Of Zhou et al., "Long–Term Expression of Human Factor IX cDNA in Rabbits," Sci China B1993 Nov; 36(11):1333–1341.

Narita, N., et al., "The Gene for Transcription Factor GATA–6 Resides on Mouse Chromosome 18 is Expressed in Myocardium and Vascular Smooth Muscle", *Genomics*, (1996), 36(2), 345–348.

Laverriere, A.C., et al., "GATA–4/5/6, A Subfamily of Three Transcription Factors Transcribed in Developing Heart and Gut", *J Biol Chem*, (1994), 269(37), 23177–23184.

Morrisey, E.E., et al., "GATA–6: A Zinc Finger Transcription Factor That is Expressed in Multiple Cell Lineages Derived from Lateral Mesoderm", Dev Biol, (1996), 177(1), 309–322.

Qureshi, S.T., et al., "Mapping of the GATA6 Gene to Mouse Chromosome 18", *Mamm Genome*, (1996), 7(9), 705–706.

Jiang, Y. And Evans, T., "The Xenopus GATA–4/5/6 Genes are Associated with Cardiac Specification and Can Regulate Cardiac–Specific Transcription During Embryogenesis", *Dev Biol*, (1996), 174(2), 258–270.

Suzuki, E., et al., "The Human GATA–6 Gene: Structure, Chromosomal Location, and Regulation of Expression by Tissue–Specific and Mitogen–Responsive Signals", *Genomics*, (1996), 38(3), 283–290.

Li et al. "Expression of the SM22alpha Promoter in Transgenic Mice Provides Evidence for Distinct Transcriptional Regulatory Programs in Vascular and Visceral Smooth Muscle Cells", *J. Biol. Chem.*, (1996), 132, 849–859.

Davis et al. (1996) The chicken vitellogenin II gene is flanked by a GATA factor–dependent estrogen response unit. Mol. Endocrinol. 10:937–944, Aug. 1996.

Verma et al. (1997) Gene therapy–promises, problems and prospects. Nature 389:239–242, Sep. 1997.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 2897 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens
    (F) TISSUE TYPE: Heart (ix) FEATURE:
    (A) NAME/KEY: CDS
    (B) LOCATION: 348..1697

(xi) SEQUENCE DESCRIPTION: SEQ ID NO:1:

```
GGAATTCCGC GCCGCCTTCC CCCATCTCTT CCTCGTCCTC CTCCTGCTCC CGGGGCGGAG    60

AGCGGGGCCC CGGCGGCGCC AGCAACTGCG GGACGCCTCA GCTCGACACG GAGGCGGCGG    120

CCGGACCCCC GGCCCGCTCG CTGCTGCTCA GTTCCTACGC TTCGCATCCC TTCGGGGCTC    180

CCCACGGACC TTCGGCGCCT GGGGTCGCGG GCCCCGGGGG CAACCTGTCG AGCTGGGAGG    240

ACTTGCTGCT GTTCACTGAC CTCGACCAAG CCGCGACCGA CAGCAAGCTG CTGTGGTCCA    300

GCCGCGGCGC CAAGCTGAGC CCCTTCGCAC CCGAGCAGCC GGAGGAG ATG TAC CAG      356
                                                  Met Tyr Gln
                                                   1

ACC CTC GCC GCT CTC TCC AGC CAG GGT CCG GCC GCC TAC GAC GGC GCG      404
Thr Leu Ala Ala Leu Ser Ser Gln Gly Pro Ala Ala Tyr Asp Gly Ala
      5                  10                  15

CCC GGC GGC TTC GTG CAC TCT GCG GCC GCG GCG GCA GCA GCC GCG GCG      452
Pro Gly Gly Phe Val His Ser Ala Ala Ala Ala Ala Ala Ala Ala Ala
 20                  25                  30                  35

GCG GCC AGC TCC CCG GTC TAC GTG CCC ACC ACC CGC GTG GGT TCC ATG      500
Ala Ala Ser Ser Pro Val Tyr Val Pro Thr Thr Arg Val Gly Ser Met
             40                  45                  50

CTG CCC GGC CTA CCG TAC CAC CTG CAG GGG TCG GGC AGT GGG CCA GCC      548
Leu Pro Gly Leu Pro Tyr His Leu Gln Gly Ser Gly Ser Gly Pro Ala
         55                  60                  65

AAC CAC GCG GGC GGC GCG GGC GCG CAC CCC GGC TGG CCT CAG GCC TCG      596
Asn His Ala Gly Gly Ala Gly Ala His Pro Gly Trp Pro Gln Ala Ser
     70                  75                  80

GCC GAC AGC CCT CCA TAC GGC AGC GGT GGC GGC GCG GCT GGC GGC GGG      644
Ala Asp Ser Pro Pro Tyr Gly Ser Gly Gly Gly Ala Ala Gly Gly Gly
 85                  90                  95

GCC GCG GGG CCT GGC GGC GCT GGC TCA GCC GCG GCG CAC GTC TCG GCG      692
Ala Ala Gly Pro Gly Gly Ala Gly Ser Ala Ala Ala His Val Ser Ala
100                 105                 110                 115

CGC TTC CCC TAC TCT CCC AGC CCG CCC ATG GCC AAC GGC GCC GCG CGG      740
Arg Phe Pro Tyr Ser Pro Ser Pro Pro Met Ala Asn Gly Ala Ala Arg
            120                 125                 130

GAG CCG GGA GGC TAC GCG GCG GCG GGC AGT GGG GGC GCG GGA GGC GTG      788
Glu Pro Gly Gly Tyr Ala Ala Ala Gly Ser Gly Gly Ala Gly Gly Val
        135                 140                 145

AGC GGC GGC GGC AGT AGC CTG GCG GCC ATG GGC GGC CGC GAG CCC CAG      836
Ser Gly Gly Gly Ser Ser Leu Ala Ala Met Gly Gly Arg Glu Pro Gln
    150                 155                 160

TAC AGC TCG CTG TCG GCC GCG CGG CCG CTG AAC GGG ACG TAC CAC CAC      884
Tyr Ser Ser Leu Ser Ala Ala Arg Pro Leu Asn Gly Thr Tyr His His
165                 170                 175

CAC CAC CAC CAC CAC CAC CAC CAT CCG AGC CCC TAC TCG CCC TAC GTG      932
His His His His His His His Pro Ser Pro Tyr Ser Pro Tyr Val
180                 185                 190                 195

GGG GCG CCA CTG ACG CCT GCC TGG CCC GCC GGA CCC TTC GAG ACC CCG      980
Gly Ala Pro Leu Thr Pro Ala Trp Pro Ala Gly Pro Phe Glu Thr Pro
            200                 205                 210
```

```
GTG CTG CAC AGC CTG CAG AGC CGC GCC GGA GCC CCG CTC CCG GTG CCC    1028
Val Leu His Ser Leu Gln Ser Arg Ala Gly Ala Pro Leu Pro Val Pro
            215                 220                 225

CGG GGT CCC AGT GCA GAC CTG CTG GAG GAC CTG TCC GAG AGC CGC GAG    1076
Arg Gly Pro Ser Ala Asp Leu Leu Glu Asp Leu Ser Glu Ser Arg Glu
                230                 235                 240

TGC GTG AAC TGC GGC TCC ATC CAG ACG CCG CTG TGG CGG CGG GAC GGC    1124
Cys Val Asn Cys Gly Ser Ile Gln Thr Pro Leu Trp Arg Arg Asp Gly
            245                 250                 255

ACC GGC CAC TAC CTG TGC AAC GCC TGC GGG CTC TAC AGC AAG ATG AAC    1172
Thr Gly His Tyr Leu Cys Asn Ala Cys Gly Leu Tyr Ser Lys Met Asn
260                 265                 270                 275

GGC CTC AGC CGG CCC CTC ATC AAG CCG CAG AAG CGC GTG CCT TCA TCA    1220
Gly Leu Ser Arg Pro Leu Ile Lys Pro Gln Lys Arg Val Pro Ser Ser
                280                 285                 290

CGG CGG CTT GGA TTG TCC TGT GCC AAC TGT CAC ACC ACA ACT ACC ACC    1268
Arg Arg Leu Gly Leu Ser Cys Ala Asn Cys His Thr Thr Thr Thr Thr
            295                 300                 305

TTA TGG CGC AGA AAC GCC GAG GGT GAA CCC GTG TGC AAT GCT TGT GGA    1316
Leu Trp Arg Arg Asn Ala Glu Gly Glu Pro Val Cys Asn Ala Cys Gly
                310                 315                 320

CTC TAC ATG AAA CTC CAT GGG GTG CCC AGA CCA CTT GCT ATG AAA AAA    1364
Leu Tyr Met Lys Leu His Gly Val Pro Arg Pro Leu Ala Met Lys Lys
            325                 330                 335

GAG GGA ATT CAA ACC AGG AAA CGA AAA CCT AAG AAC ATA AAT AAA TCA    1412
Glu Gly Ile Gln Thr Arg Lys Arg Lys Pro Lys Asn Ile Asn Lys Ser
340                 345                 350                 355

AAG ACT TGC TCT GGT AAT AGC AAT AAT TCC ATT CCC ATG ACT CCA ACT    1460
Lys Thr Cys Ser Gly Asn Ser Asn Asn Ser Ile Pro Met Thr Pro Thr
                360                 365                 370

TCC ACC TCT TCT AAC TCA GAT GAT TGC AGC AAA AAT ACT TCC CCC ACA    1508
Ser Thr Ser Ser Asn Ser Asp Asp Cys Ser Lys Asn Thr Ser Pro Thr
            375                 380                 385

ACA CAA CCT ACA GCC TCA GGG GCG GGT GCC CCG GTG ATG ACT GGT GCG    1556
Thr Gln Pro Thr Ala Ser Gly Ala Gly Ala Pro Val Met Thr Gly Ala
                390                 395                 400

GGA GAG AGC ACC AAT CCC GAG AAC AGC GAG CTC AAG TAT TCG GGT CAA    1604
Gly Glu Ser Thr Asn Pro Glu Asn Ser Glu Leu Lys Tyr Ser Gly Gln
405                 410                 415

GAT GGG CTC TAC ATA GGC GTC AGT CTC GCC TCG CCG GCC GAA GTC ACG    1652
Asp Gly Leu Tyr Ile Gly Val Ser Leu Ala Ser Pro Ala Glu Val Thr
420                 425                 430                 435

TCC TCC GTG CGA CCG GAT TCC TGG TGC GCC CTG GCC CTG GCC TGAGCCCACG 1704
Ser Ser Val Arg Pro Asp Ser Trp Cys Ala Leu Ala Leu Ala
                440                 445                 450

CCGCCAGGAG GCAGGGAGGG CTCCGCCGCG GGCCTCACTC CACTCGTGTC TGCTTTTGTG  1764

CAGCGGTCCA GACAGTGGCG ACTGCGCTGA CAGAACGTGA TTCTCGTGCC TTTATTTTGA  1824

AAGAGATGTT TTTCCCAAGA GGCTTGCTGA AAGAGTGAGA GAAGATGGAA GGGAAGGGCC  1884

AGTGCAACTG GGCGCTTGGG CCACTCCAGC CAGCCCGCCT CCGGGGCGGA CCCTGCTCCA  1944

CTTCCAGAAG CCAGGACTAG GACCTGGGCC TTGCCTGCTA TGGAATATTG AGAGAGATTT  2004

TTTAAAAAAG ATTTTGCATT TTGTCCAAAA TCATGTGCTT CTTCTGATCA ATTTTGGTTG  2064

TTCCAGAATT TCTTCATACC TTTTCCACAT CCAGATTTCA TGTGCGTTCA TGGAGAAGAT  2124

CACTTGAGGC CATTTGGTAC ACATCTCTGG AGGCTGAGTC GGTTCATGAG GTCTCTTATC  2184

AAAAATATTA CTCAGTTTGC AAGACTGCAT TGTAACTTTA ACATACACTG TGACTGACGT  2244

TTCTCAAAGT TCATATTGTG TGGCTGATCT GAAGTCAGTC GGAATTTGTA AACAGGGTAG  2304
```

```
CAAACAAGAT ATTTTTCTTC CATGTATACA ATAATTTTTT TAAAAAGTGC AATTTGCGTT    2364

GCAGCAATCA GTGTTAAATC ATTTGCATAA GATTTAACAG CATTTTTTAT AATGAATGTA    2424

AACATTTTAA CTTAATGGTA CTTAAAATAA TTTAAAAGAA AAATGTTAAC TTAGACATTC    2484

TTATGCTTCT TTTACAACTA CATCCCATTT TATATTTCCA ATTGTTAAAG AAAAATATTT    2544

CAAGAACAAA TCTTCTCTCA GGAAAATTGC CTTTCTCTAT TTGTTAAGAA TTTTTATACA    2604

AGAACACCAA TATACCCCCT TTATTTTACT GTGGAATATG TGCTGGAAAA ATTGCAACAA    2664

CACTTTACTA CCTAACGGAT AGCATTTGTA AATACTCTAG GTATCTGTAA ACACTCTGAT    2724

GAAGTCTGTA TAGTGTGACT AACCCACAGG CAGGTTGGTT TACATTAATT TTTTTTTTGA    2784

ATGGGATGTC CTATGGAAAC CTATTTCACC AGAGTTTTAA AAATAAAAG GGTATTGTTT     2844

TGTCTTCTGT AAAAAAAAAA AAAAAAAAAA AAAAAAAAAA AAAAAAAAA AAA            2897
```

(2) INFORMATION FOR SEQ ID NO:2:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:2:

```
Met Tyr Gln Thr Leu Ala Ala Leu Ser Ser Gln Gly Pro Ala Tyr
 1               5                  10                  15

Asp Gly Ala Pro Gly Gly Phe Val His Ser Ala Ala Ala Ala Ala
            20                  25                  30

Ala Ala Ala Ala Ala Ser Ser Pro Val Tyr Val Pro Thr Thr Arg Val
        35                  40                  45

Gly Ser Met Leu Pro Gly Leu Pro Tyr His Leu Gln Gly Ser Gly Ser
    50                  55                  60

Gly Pro Ala Asn His Ala Gly Ala Gly Ala His Pro Gly Trp Pro
65                  70                  75                  80

Gln Ala Ser Ala Asp Ser Pro Tyr Gly Ser Gly Gly Ala Ala
            85                  90                  95

Gly Gly Gly Ala Ala Gly Pro Gly Gly Ala Gly Ser Ala Ala Ala His
        100                 105                 110

Val Ser Ala Arg Phe Pro Tyr Ser Pro Ser Pro Met Ala Asn Gly
    115                 120                 125

Ala Ala Arg Glu Pro Gly Gly Tyr Ala Ala Ala Gly Ser Gly Gly Ala
        130                 135                 140

Gly Gly Val Ser Gly Gly Ser Ser Leu Ala Ala Met Gly Gly Arg
145                 150                 155                 160

Glu Pro Gln Tyr Ser Ser Leu Ser Ala Ala Arg Pro Leu Asn Gly Thr
            165                 170                 175

Tyr His His His His His His His His His Pro Ser Pro Tyr Ser
            180                 185                 190

Pro Tyr Val Gly Ala Pro Leu Thr Pro Ala Trp Pro Ala Gly Pro Phe
        195                 200                 205

Glu Thr Pro Val Leu His Ser Leu Gln Ser Arg Ala Gly Ala Pro Leu
    210                 215                 220

Pro Val Pro Arg Gly Pro Ser Ala Asp Leu Leu Glu Asp Leu Ser Glu
225                 230                 235                 240

Ser Arg Glu Cys Val Asn Cys Gly Ser Ile Gln Thr Pro Leu Trp Arg
            245                 250                 255
```

```
Arg Asp Gly Thr Gly His Tyr Leu Cys Asn Ala Cys Gly Leu Tyr Ser
            260                 265                 270

Lys Met Asn Gly Leu Ser Arg Pro Leu Ile Lys Pro Gln Lys Arg Val
            275                 280                 285

Pro Ser Ser Arg Arg Leu Gly Leu Ser Cys Ala Asn Cys His Thr Thr
            290                 295                 300

Thr Thr Thr Leu Trp Arg Arg Asn Ala Glu Gly Glu Pro Val Cys Asn
305                 310                 315                 320

Ala Cys Gly Leu Tyr Met Lys Leu His Gly Val Pro Arg Pro Leu Ala
            325                 330                 335

Met Lys Lys Glu Gly Ile Gln Thr Arg Lys Arg Lys Pro Lys Asn Ile
            340                 345                 350

Asn Lys Ser Lys Thr Cys Ser Gly Asn Ser Asn Ser Ile Pro Met
            355                 360                 365

Thr Pro Thr Ser Thr Ser Ser Asn Ser Asp Asp Cys Ser Lys Asn Thr
            370                 375                 380

Ser Pro Thr Thr Gln Pro Thr Ala Ser Gly Ala Gly Ala Pro Val Met
385                 390                 395                 400

Thr Gly Ala Gly Glu Ser Thr Asn Pro Glu Asn Ser Glu Leu Lys Tyr
            405                 410                 415

Ser Gly Gln Asp Gly Leu Tyr Ile Gly Val Ser Leu Ala Ser Pro Ala
            420                 425                 430

Glu Val Thr Ser Ser Val Arg Pro Asp Ser Trp Cys Ala Leu Ala Leu
            435                 440                 445

Ala
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: modified_base (deoxyinosine)
        (B) LOCATION: 6

(ix) FEATURE:
        (A) NAME/KEY: modified_base (deoxyinosine)
        (B) LOCATION: 9

(ix) FEATURE:
        (A) NAME/KEY: modified_base (deoxyinosine)
        (B) LOCATION: 18

(xi) SEQUENCE DESCRIPTION: SEQ ID NO:3:

GARGCNMGNG ARTGYGTNAA YTG                                      23

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (ix) FEATURE:
             (A) NAME/KEY: modified_base (deoxyinosine)
             (B) LOCATION: 4

(ix) FEATURE:
             (A) NAME/KEY: modified_base (deoxyinosine)
             (B) LOCATION: 7

(ix) FEATURE:
             (A) NAME/KEY: modified_base (deoxyinosine)
             (B) LOCATION: 13

(ix) FEATURE:
             (A) NAME/KEY: modified_base (deoxyinosine)
             (B) LOCATION: 22

(xi) SEQUENCE DESCRIPTION: SEQ ID NO:4:

RTANARNCCR CANGCRTTRC ANAC                                                24

(2) INFORMATION FOR SEQ ID NO:5:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CGTGAACTGT GGCTCCATCC A                                                   21

(2) INFORMATION FOR SEQ ID NO:6:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

AGTTGGCACA GGACAGTCCA A                                                   21

(2) INFORMATION FOR SEQ ID NO:7:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

TGGAGGACCT GTCCGAGAGC CGCGAGACCT T                                        31

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

GTCTCGCGGC TCTCGGACAG GTCCTCC                          27

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

GCCGGGCAAC TGATAAGGAT TCCCA                           25

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GACCGGGCAA CTGCGAAGGA TTCCCA                         26

GATA-6 TRANSCRIPTION FACTOR: COMPOSITIONS AND METHODS

RELATED APPLICATIONS

This application claims priority under 35 USC §119(e) from U.S. patent application Ser. No. 60/025,574, filed on Sep. 6, 1996, entitled GATA-6 TRANSCRIPTION FACTOR: COMPOSITIONS AND METHODS, the disclosure of which is incorporated herein by reference.

FIELD OF THE INVENTION

This invention relates to methods and compositions for treating excessive vascular smooth muscle cell proliferation. More particularly, this invention relates to administering GATA-6 to a subject diagnosed as having a condition that is associated with excessive vascular smooth muscle cell proliferation (e.g., arteriosclerosis).

BACKGROUND OF THE INVENTION

Arteriosclerosis is a disease that is characterized by a thickening and hardening of regions of an arterial wall. A particular type of arteriosclerosis is atherosclerosis, which affects the large arteries and is often the basis for coronary artery disease, aortic aneurysm, arterial disease of the lower extremities, and cerebrovascular disease. Atherosclerosis is characterized by the formation of fibrous plaques that contain a large number of smooth muscle cells, macrophages, collagen, extracellular lipid, and necrotic cell debris. The accumulation of material in a fibrous plaque results in narrowing of the blood vessel lumen which, in turn, restricts arterial blood flow. When the fibrous plaques become sufficiently large to block blood flow completely, the organs that are supplied by the artery undergo ischemia and necrosis. The accumulation of fibrous plaques also weaken the artery, an event which frequently results in rupture of the intima, aneurysm and hemorrhage. Moreover, fragments of the fibrous plaque may detach and form arterial emboli that can precipitate an aortic aneurysm or arterial disease of the lower extremities.

To date, the most frequently used methods for treating atherosclerosis include surgical procedures, drug therapies, and combinations of the foregoing. In general, the drug therapies for treating atherosclerosis are designed to prevent or reduce the accumulation of plaque material. For example, drugs such as diuretics, anti-adrenergic agents, vasodilators, angiotensin-converting enzyme inhibitors, renin inhibitors, and calcium channel antagonists have been used to treat conditions such as hypertension, hyperlipidemia, and hypercholesterolemia, which contribute to the development of atherosclerosis. Surgical methods for treating atherosclerosis include coronary bypass surgery, atherectomy, laser procedures, ultrasonic procedures, and balloon angioplasty. Such methods involve significant risk (e.g., of infection, death) to the patient and, even if successful, fibrous plaque formation frequently occurs at the site of vascular anastomoses, causing reocclusion of the surgically-treated vessel.

In view of the foregoing, a need still exists for improved drug therapies to replace or supplement the existina methods for treating atherosclerosis and related conditions that are mediated by fibrous plaque formation. Preferably, such drug therapies would be designed to reduce or prevent plaque formation at its earliest stages.

SUMMARY OF THE INVENTION

The invention involves the discovery that a human GATA-6 transcription factor ("GATA-6") is expressed in differentiated human vascular smooth muscle cells ("VSMC") and that the expression of GATA-6 is significantly lower in proliferating vascular smooth muscle cells than in differentiated vascular smooth muscle cells. Applicant further has discovered that the expression of human GATA-6 in differentiated vascular smooth muscle cells prevents mitogen stimulated proliferation of these cells. In view of these discoveries, it is believed that GATA-6 can be used to as a drug to inhibit vascular smooth muscle cell proliferation and, in particular, to treat conditions (e.g., atherosclerosis) that result from excessive smooth muscle cell proliferation.

GATA-6 is the most recently identified member of the GATA family of transcription factors (GATA-1, 2, 3, 4, 5, and 6). GATA-6 reportedly is expressed in the heart during early embryonic development, but its expression is down regulated in this organ during late embryonic development. In contrast to the literature reports of a role for GATA-6 in regulating cardiac specific genes (Laverriere, A. C., et al., Journal of Biological Chemistry, v. 269, p. 23177–23184 (1994)), Applicant describes herein a new function for GATA-6, namely, the ability to prevent or reduce excessive vascular smooth muscle cell proliferation. Accordingly, the instant invention is directed to compositions and methods that are based upon the discovery of this newly-discovered function.

According to one aspect of the invention, a method for treating a subject diagnosed as having a condition associated with excessive vascular smooth muscle cell proliferation is provided. The method involves administering to the subject an isolated GATA-6 molecule (a "GATA-6 nucleic acid" or a "GATA-6 protein") in an amount effective to prevent or reduce excessive vascular smooth muscle cell proliferation in vivo. Preferably, the GATA-6 molecule is administered to the subject in conjunction with a method for treating an arteriosclerotic condition. The method for treating an arteriosclerotic condition may be a surgical method or a drug therapy (e.g., gene therapy). In one embodiment, the drug therapy involves administering to the subject a cytostatic molecule or a cytokine (e.g., a cytokine that promotes endothelial cell proliferation). Accordingly, the compositions and methods of the invention are useful for replacing existing drug therapies, as well as for improving the effectiveness of existing therapies for treating conditions that are characterized by excessive vascular smooth muscle cell proliferation. In general, such conditions are diagnosed by detecting the presence of fibrous plaques in the blood vessel walls of the subject.

In the particularly preferred embodiments, the GATA-6 molecule is delivered directly to the site at which there is excessive vascular smooth muscle cell proliferation, i.e., the site of vascular injury. For example, this can be accomplished by attaching a GATA-6 nucleic acid or a GATA-6 protein to the surface of a balloon catheter; inserting the catheter into the subject until the balloon portion is located at the site of an occlusion; and inflating the balloon to contact the balloon surface with the vessel wall at the site of the occlusion. In this manner, the compositions can be targeted to particular sites within a vessel to prevent or reduce smooth muscle cell proliferation at these sites. Optionally, the GATA-6 molecule is delivered in combination with a cytostatic molecule (e.g., GAX); a cytokine that promotes endothelial cell proliferation, or a nucleic acid encoding one or more of the foregoing molecules.

A "GATA-6 molecule" embraces a "GATA-6 nucleic acid" and a "GATA-6 protein". As used herein, a "GATA-6 nucleic acid" refers to a nucleic acid molecule which: (1)

hybridizes under stringent conditions to a nucleic acid having the sequence of SEQ. ID. No. 1 (the GATA-6 molecule isolated from human vascular smooth muscle cells) and (2) codes for a GATA-6 protein that prevents or reduces the proliferation of vascular smooth muscle cells. The preferred GATA-6 nucleic acid has the sequence of SEQ. ID. No. 1. Thus, homologs and alleles of a nucleic acid having the sequence of SEQ. ID. No. 1 also are embraced within the definition of a "GATA-6 nucleic acid". In addition, the GATA-6 nucleic acids of the invention include nucleic acids which code for the GATA-6 protein having the sequence of SEQ. ID 2, but which differ from the sequence of SEQ. ID. No. 1 in codon sequence due to the degeneracy of the genetic code. The invention also embraces isolated functionally equivalent variants, analogs and fragments of the foregoing nucleic acids; proteins and peptides coded for by any of the foregoing nucleic acids; and complements of the foregoing nucleic acids.

As used herein, a "GATA-6 protein" refers to a protein that is coded for by a GATA-6 nucleic acid. GATA-6 proteins are useful for reducing or preventing excessive vascular smooth muscle cell proliferation. The preferred GATA-6 protein of the invention has the amino acid sequence of SEQ. ID NO. 2. GATA-6 proteins further embrace functionally equivalent variants, analogs, and fragments of SEQ. ID NO. 2, provided that the variants, analogs, and fragments reduce or prevent vascular smooth muscle cell proliferation. The invention also embraces proteins and peptides coded for by any of the foregoing nucleic acids. For example, the invention embraces proteins and polypeptides which are coded for by unique fragments of the foregoing nucleic acids. Such proteins and polypeptides are useful, for example, as immunogens for generating antibodies to unique epitopes of the GATA-6 protein.

According to another aspect of the invention, a composition containing the above-described GATA-6 nucleic acid is provided. Preferably, the GATA-6 nucleic acid is operably linked to a gene expression sequence that mediates expression of the GATA-6 nucleic acid in a eukaryotic cell. More preferably, the GATA-6 nucleic acid is contained in a biological vector (e.g., an expression vector such a viral vector or a plasmid), and/or is associated with a chemical/physical vector (e.g., a liposome, a microsphere) that facilitates delivery to and/or uptake by the target cell (e.g., a vascular smooth muscle cell) of the GATA-6 molecule.

According to another aspect of the invention, a composition containing the above-described GATA-6 protein is provided. The preferred GATA-6 protein-containing composition contains a GATA-6 protein that has the sequence of SEQ. ID. NO. 2. Optionally, the composition further contains a chemical/physical vector (e.g., a micro sphere) for facilitating delivery of the GATA-6 protein to the cell and/or uptake of this molecule by the target cell.

According to yet another aspect of the invention, a method for reducing or preventing the proliferation of a tumor cell is provided. The method involves the step of contacting the tumor cell that exhibits excessive proliferation with respect to a normal cell of the same cell type with a GATA-6 molecule in an amount effective to prevent or reduce excessive tumor cell proliferation.

The above-described compositions optionally include a pharmaceutically acceptable carrier. The above-described compositions also may include a cytostatic molecule and/or a cytokine for further enhancing the therapeutic effect of the GATA-6 molecule. In general, the cytokines of the invention that are useful for enhancing the therapeutic effect of a GATA-6 molecule are cytokines that promote endothelial cell proliferation.

These and other aspects of the invention, as well as various advantages and utilities, will be more apparent with reference to the detailed description of the preferred embodiments.

DETAILED DESCRIPTION OF THE INVENTION

The present invention in one aspect involves the use of an isolated GATA-6 molecule to prevent or reduce excessive vascular smooth muscle cell proliferation. As used herein, "prevent" refers to inhibiting vascular smooth muscle cell proliferation, as well as to inhibiting an increase in the amount of vascular smooth muscle cell proliferation. Unlike cardiac and skeletal muscle cells, vascular smooth muscle cells do not terminally differentiate and can reversibly modulate their phenotype and cell cycle activity in response to growth factor stimulation. Differentiated vascular smooth muscle cells are quiescent and express high levels of GATA-6. It has been found that GATA-6, which is expressed at a high level in differentiated vascular smooth muscle cells, is rapidly downregulated when these cells are activated by a mitogen. Mitogen stimulation of these cells promotes the development of a proliferative phenotype which expresses much lower levels of GATA-6. Cells having the proliferative phenotype are believed to be similar to the vascular smooth muscle cells that are present in vessel wall lesions.

Prior to the instant invention, it was not known that GATA-6 was expressed in vascular smooth muscle cells or that GATA-6 expression could be downregulated by growth factors. These findings were surprising in view of the significant research effort directed to defining the tissue specific expression and function of the various members of the GATA transcription factor family. Although Applicant does not wish to be bound by any particular theory, it is believed that GATA-6 modifies the proliferative state of a vascular smooth muscle cell by one or both of the following two mechanisms. It is believed that GATA-6 may function by coordinating the expression of vascular smooth muscle cell genes with cell cycle progression during the initial phases of phenotypic modulation. Exemplary genes which are expressed in vascular smooth muscle cells that include a conserved GATA-binding site within their promoter regions and that may be regulated by GATA-6 include elastin, PAI-1, VCAM1 and vimentin. Alternatively or additionally, the level of GATA-6 expression may modulate vascular smooth muscle cell cycle activity by directly modulating the expression of cell cycle regulatory proteins.

In one aspect, the invention is directed to a method for treating a subject diagnosed as having a condition associated with excessive vascular smooth muscle cell or other cell (e.g., a tumor cell) proliferation. The method involves administering to the subject an isolated GATA-6 molecule in an amount effective to prevent or reduce excessive vascular smooth muscle cell or other cell proliferation in vivo.

A subject, as used herein, refers to any mammal that may be susceptible to the condition associated with excessive vascular smooth muscle cell or other cell proliferation. Preferably, the subject is a human. Excessive, with respect to vascular smooth muscle cell or other cell proliferation, refers to an amount of vascular smooth muscle cell proliferation which is (1) greater than the amount of proliferation that occurs in a normal, healthy subject; and (2) results in an adverse medical condition. Exemplary conditions that are caused by excessive vascular smooth muscle cell proliferation are known to those of ordinary skill in the art and include, but are not limited to, the following diseases: arteriosclerosis, including atherosclerosis and post interventional restenosis.

A "GATA-6 molecule", as used herein, embraces both "GATA-6 nucleic acids" and "GATA-6 proteins" (discussed below). GATA-6 molecules are capable of reducing or preventing the proliferation of vascular smooth muscle cells in vivo and in vitro. GATA-6 molecules are also capable of reducing or preventing the proliferation of normal fibroblasts, transformed cells (such as p53(–) cells), and other cells which exhibit excessive proliferation with respect to a normal cell of the same cell type (e.g., tumor cells). The term "isolated", as used herein in reference to a nucleic acid molecule, means a nucleic acid sequence: (i) amplified in vitro by, for example, polymerase chain reaction (PCR); (ii) synthesized by, for example, chemical synthesis; (iii) recombinatly produced by cloning; or (iv) purified, as by cleavage and gel separation. The term "isolated", as used herein in reference to a protein, means a polypeptide encoded by an isolated nucleic acid sequence, as well as polypeptides synthesized by, for example, chemical synthetic methods, and polypeptides separated from biological materials, and then purified using conventional protein analytical procedures.

A "GATA-6 nucleic acid", as used herein, refers to a nucleic acid molecule which: (1) hybridizes under stringent conditions to a nucleic acid having the sequence of SEQ. ID. No. 1 and (2) codes for a GATA-6 protein (i.e., a protein which prevents or reduces vascular smooth muscle cell proliferation). The preferred GATA-6 nucleic acid has the nucleic acid sequence of SEQ. ID No. 1. The GATA-6 nucleic acids of the invention also include homologs and alleles of a nucleic acid having the sequence of SEQ. ID. No. 1, as well as functionally equivalent variants, analogs and fragments of the foregoing nucleic acids. "Functionally equivalent", in reference to a GATA-6 nucleic acid variant, analog or fragment, refers to a nucleic acid that codes for a GATA-6 protein that is capable of preventing or reducing smooth muscle cell proliferation. GATA-6 nucleic acids further embrace nucleic acid molecules which code for the GATA-6 protein having the sequence of SEQ. ID 2 but which differ from the sequence of SEQ. ID. No. 1 in codon sequence due to the degeneracy of the genetic code. The invention further embraces unique fragments (which may, or may not be "functional" with respect to encoding a GATA-6 protein) and complements of the foregoing nucleic acids. Such unique fragments can be used, for example, as probes in hybridization assays and as primers in a polymerase chain reaction (PCR).

The GATA-6 nucleic acid molecules of the invention can be identified by conventional techniques, e.g., by identifying nucleic acid sequences which code for GATA-6 proteins and which hybridize to a nucleic acid molecule having the sequence of SEQ. ID. No. 1 under stringent conditions. The term "stringent conditions", as used herein, refers to parameters with which the art is familiar. More specifically, stringent conditions, as used herein, refer to hybridization at 65° C. in hybridization buffer (3.5 ×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2× SSC at room temperature and then at 0.1× SSC/0.1× SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the GATA-6 nucleic acid of the invention. The skilled artisan also is familiar with the methodology for screening cells and libraries for the expression of molecules, such as GATA-6, can be isolated, following by isolation of the pertinent nucleic acid molecule and sequencing. In screening for GATA-6 nucleic acid sequences, a Southern blot may be performed using the foregoing conditions, together with a radioactive probe. After washing the membrane to which the DNA is finally transferred, the membrane can be placed against x-ray film to detect the radioactive signal.

In general, homologs and alleles typically will share at least 40% nucleotide identity with SEQ. ID. No. 1; in some instances, will share at least 50% nucleotide identity; and in still other instances, will share at least 60% nucleotide identity. Watson-Crick complements of the foregoing nucleic acids are also embraced by the invention. SEQ. ID No. 1 shares a substantial degree of sequence homology with the other members of the GATA transcription factor family (e.g., GATA-4, GENBANK Accession No. S78666 and GATA-5 GENBANK Accession No. U11888). Accordingly, such family members are considered "a GATA-6 nucleic acid" within the meaning of the instant invention, provided that such family members prevent or reduce vascular smooth muscle cell proliferation as determined, for example, using the screening assays described herein. The preferred homologs have at least 70% sequence homology to SEQ. ID. No. 1. More preferably the preferred homologs have at least 80% and most preferably at least 90% sequence homology to SEQ. ID. No. 1.

The invention also includes degenerate nucleic acids which include alternative codons to those present in the naturally occurring nucleic acid that codes for the human GATA-6 protein. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring isolated nucleic acids in codon sequence due to the degeneracy of the genetic code.

The invention also provides isolated unique fragments of SEQ. ID. No. 1 and complements of the foregoing GATA-6 nucleic acids. A unique fragment is one that is a 'signature' for the larger nucleic acid. It, for example, is long enough to assure that its precise sequence is not found in molecules outside of the GATA-6 gene. Unique fragments can be used as probes in Southern blot assays to identify family members or can be used in amplification assays such as those employing PCR. As known to those skilled in the art, large probes such as 200 base pair (BP) or more are preferred for certain uses such as Southern blots, while smaller fragments will be preferred for uses such as PCR. The fragments are also useful as probes for mRNA in Northern blot analysis. Unique fragments also can be used to produce fusion proteins for generating antibodies or for generating immunoassay components. Unique fragments are also useful for a variety of assays to determine the protein binding regions of the nucleic acid, such as gel shift assays and can be cloned into reporter constructs such as a chloramphenicol acetyl transferase (CAT) vector to determine the active promoter and enhancer regions. Likewise, unique fragments can be employed to produce fragments of the GATA-6 protein, such as the zinc finger portion, useful, for example, as a competitive inhibitor of the binding interaction between the GATA-6 protein and the specific DNA binding site for the GATA-6 protein (the binding site includes at least the following four nucleotides: GATA). It is useful to inhibit the binding interaction, for example, to prevent transactivation of a gene having a GATA-6 binding sequence in its promoter region. Complements of unique fragments further can be used as antisense molecules to inhibit the expression of the GATA-6 of the invention, particularly for therapeutic purposes as described in greater detail below.

As will be recognized by those skilled in the art, the size of the unique fragment will depend upon its conservancy in the genetic code. Thus, some regions of SEQ. ID. No. 1, will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long). Virtually any segment of SEQ. ID. No. 1, that is 18 or more nucleotides in length will be unique. Those skilled in the art are well versed in methods for selecting such sequences, typically on the basis of the ability of the unique fragment to selectively distinguish the sequence of interest from other family members. A comparison of the sequence of the fragment to those on known data bases typically is all that is necessary, although in vitro confirmatory hybridization and sequencing analysis optionally is performed.

The invention also embraces antisense oligonucleotides that selectively bind to a GATA-6 nucleic acid molecule, to reduce the expression of GATA-6 and thereby stimulate the proliferation of smooth muscle cells. Antisense oligonucleotides are useful, for example, for preparing an animal model of a condition that is characterized by excessive vascular smooth muscle cell proliferation. Such animal models can be used in screening assays for identifying therapeutic drugs which prevent or reduce the excessive vascular smooth muscle cell proliferation.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target mammalian cell gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or RNA (e.g., mRNA) transcripts, in preferred embodiments the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., *Cell Mol. Neurobiol.* 14(5):439–457 (1994)) and at which proteins are not expected to bind. The selective binding of the antisense oligonucleotide to a mammalian target cell nucleic acid effectively decreases or eliminates the transcription or translation of the mammalian target cell nucleic acid molecule. Reduction in transcription or translation of the nucleic acid molecule is desirable in preparing an animal model for further defining the role played by the mammalian target cell nucleic acid in modulating an adverse medical condition.

The GATA-6 nucleic acid, in one embodiment, is operably linked to a gene expression sequence which directs the expression of the GATA-6 nucleic acid within a eukaryotic cell. The "gene expression sequence" is any regulatory nucleotide sequence, such as a promoter sequence or promoter-enhancer combination, which facilitates the efficient transcription and translation of the GATA-6 nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined GATA-6 nucleic acid. The gene expression sequences optionally includes enhancer sequences or upstream activator sequences as desired.

Preferably, the GATA-6 nucleic acid of the invention is linked to a gene expression sequence which permits expression of the GATA-6 nucleic acid in a smooth muscle cell. More preferably, the gene expression sequence permits expression of the GATA-6 nucleic acid in a human vascular smooth muscle cell and does not permit expression of the GATA-6 nucleic acid in hepatocytes and other normally proliferative cell types because it is undesirable to interfere with the normal proliferation of these cells. A sequence which permits expression of the GATA-6 nucleic acid in a human vascular smooth muscle cell is one which is selectively active in vascular smooth muscle cells and thereby causes the expression of the GATA-6 nucleic acid in these cells. The following promoters can be used to express the GATA-6 nucleic acid in human vascular smooth muscle cells: myosin heavy chain promoter and smooth muscle 22α promoter. Those of ordinary skill in the art will be able to easily identify alternative promoters that are capable of expressing a GATA-6 nucleic acid in a vascular smooth muscle cell.

The GATA-6 nucleic acid sequence and the gene expression sequence are said to be "operably linked" when they are covalently linked in such a way as to place the transcription and/or translation of the GATA-6 coding sequence under the influence or control of the gene expression sequence. If it is desired that the GATA-6 sequence be translated into a functional protein, two DNA sequences are said to be operably linked if induction of a promoter in the 5' gene expression sequence results in the transcription of the GATA-6 sequence and if the nature of the linkage between the two DNA sequences does not (1) result in the introduction of a frame-shift mutation, (2) interfere with the ability of the promoter region to direct the transcription of the GATA-6 sequence, or (3) interfere with the ability of the corresponding RNA transcript to be translated into a protein. Thus, a gene expression sequence would be operably linked to a GATA-6 nucleic acid sequence if the gene expression sequence were capable of effecting transcription of that GATA-6 nucleic acid sequence such that the resulting transcript might be translated into the desired protein or polypeptide.

The GATA-6 nucleic acid of the invention can be delivered to the vascular smooth muscle cell alone or in association with a vector. In its broadest sense, a "vector" is any vehicle capable of facilitating: (1) delivery of a GATA-6 molecule to a target cell or (2) uptake of a GATA-6 molecule by a target cell. Preferably, the vectors transport the GATA-6 molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a GATA-6 nucleic acid or a GATA-6 protein) can be selectively delivered to a vascular smooth muscle cell in, e.g., the arterial wall. In general, the vectors useful in the invention are divided into two classes: biological vectors and chemical/physical vectors. Biological vectors are useful for delivery/uptake of GATA-6 nucleic acids to/by a target cell. Chemical/physical vectors are useful for delivery/uptake of GATA-6 nucleic acids or GATA-6 proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retrovirus, such as moloney murine leukemia virus; harvey murine sarcoma virus; murine mammary tumor virus; rouse sarcoma virus; adenovirus; adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman C. O., New York (1990) and Murry, E. J. Ed. "Methods in Molecular Biology," vol. 7, Humana Press, Inc., Cliffton, N.J. (1991).

A particularly preferred retroviral vector is the vector derived from the moloney murine leukemia virus, as described in Nabel, E.G., et al., *Science*, v. 249, p. 1285–1288 (1990). These vectors reportedly were effective for the delivery of genes to all three layers of the arterial wall, including the media, which is composed of smooth muscle cells. Other preferred vectors are disclosed in Flugelman, et al., *Circulation*, v. 85, p. 1110–1117 (1992).

Another preferred virus for certain applications is the adeno-associated virus, a double-stranded DNA virus. The adeno-associated virus can be engineered to be replication—deficient and is capable of infecting a wide range of cell types and species. It further has advantages, such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In addition to the biological vectors, chemical/physical vectors may be used to deliver a GATA-6 molecule to a target cell and facilitate uptake thereby. As used herein, a "chemical/physical vector" refers to a natural or synthetic molecule, other than those derived from bacteriological or viral sources, capable of delivering the isolated GATA-6 molecule to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0µ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the vascular cell wall, by coupling the liposome to a specific ligand such as a monoclonal antibody, sugar, glycolipid, or protein. Ligands which may be useful for targeting a liposome to the vascular wall include, but are not limited to: the viral coat protein of the Hemagglutinating virus of Japan. Additionally, the vector may be coupled to a nuclear targeting peptide, which will direct the GATA-6 nucleic acid to the nucleus of the host cell.

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylarnrnonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985).

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the GATA-6 nucleic acids described herein are encapsulated or dispersed within the biocompatible, preferably biodegradable polymeric matrix disclosed in PCT/US/03307. The polymeric matrix preferably is in the form of a micro particle such as a micro sphere (wherein the GATA-6 nucleic acid is dispersed throughout a solid polymeric matrix) or a microcapsule (wherein the GATA-6 nucleic acid is stored in the core of a polymeric shell). Other forms of the polymeric matrix for containing the GATA-6 nucleic acid include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver the GATA-6 nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the GATA-6 nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly (butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in *Macromolecules*, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate). Thus, the invention provides a composition of the above-described GATA-6 molecules for use as a medicament, methods for preparing the medicament and methods for the sustained release of the medicament in vivo. In the preferred embodiments, the GATA-6 nucleic acid has the nucleic acid sequence of SEQ. ID NO. 1. Preferably, the GATA-6 nucleic acid is operably linked to a gene expression sequence to permit expression of the GATA-6 nucleic acid in the target cell. The preferred GATA-6 protein has the amino acid sequence of SEQ. ID NO. 2.

Compaction agents also can be used alone, or in combination with, a biological or chemical/physical vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the isolated GATA-6 nucleic acid in a form that is more efficiently taken up by the cell or, more preferably, in combination with one or more of the above-described vectors.

Other exemplary compositions that can be used to facilitate uptake by a target cell of the GATA-6 nucleic acids include calcium phosphate and other chemical mediators of intracellular transport, microinjection compositions, electroporation and homologous recombination compositions (e.g., for integrating a GATA-6 nucleic acid into a preselected location within the target cell chromosome).

The GATA-6 nucleic acids code for a GATA-6 protein. The preferred GATA-6 protein has an amino acid sequence of SEQ. ID NO. 2. GATA-6 proteins also embrace functionally equivalent variants, analogs, and fragments of SEQ. ID NO. 2, provided that the variants, analogs, and fragments prevent or reduce vascular smooth muscle cell proliferation.

A "functionally equivalent variant" of SEQ. ID NO. 2 is capable of preventing or reducing the proliferation of a vascular smooth muscle cell in vitro or in vivo. An in vitro proliferation assay (see, e.g., the proliferation assay provided in the Examples) can be used as a screening assay to measure the ability of a polypeptide to prevent or reduce vascular smooth muscle cell proliferation in vitro and is predictive of the ability of the polypeptide to inhibit the proliferation of vascular smooth muscle cells in vivo. Exemplary "functionally equivalent variants" of SEQ. ID. No. 2 includes fragments of SEQ. ID. No. 2, as well as polypeptide analogs of SEQ. ID. No. 2 which contain conservative amino acid substitutions, provided that the polypeptide variants and analogs are capable of preventing or reducing vascular smooth muscle cell proliferation.

It will be appreciated by those skilled in the art that various modifications of the GATA-6 protein having the sequence of SEQ. ID. No. 2 can be made without departing from the essential nature of the invention. Accordingly, it is intended that polypeptides which have the amino acid sequence of SEQ. ID NO. 2 but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids with the following groups: (1) MILV; (2) FYW; (3) KRH; (4) AG; (5) ST; (6) QN; and, (7) ED. Fusion proteins, in which a peptide of the invention is coupled to a solid support (such as a polymeric bead), a carrier molecule (such as keyhole limpet hemocyanin), or a reporter group (such as radiolabel or other tag), also are embraced within the invention.

When used therapeutically, the isolated GATA-6 molecules of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg//kg to about 20 mg/kg, in one or more dose administrations daily, for one or more days.

The therapeutically effective amount of the isolated GATA-6 molecule is that amount effective to prevent or reduce vascular smooth muscle or other cell proliferation as determined by, for example, a standard test known in the art. For example, thymidine incorporation assays and proliferating cell nuclear antigen (PCNA) assays can be used to assess vascular smooth muscle cell proliferation.

Optionally, the isolated GATA-6 molecule is administered to the subject in combination with a method for treating an arteriosclerotic condition. An arteriosclerotic condition, as used herein, is a term of art that refers to classical atherosclerosis, accelerated atherosclerosis, atherosclerotic lesions and other physiological conditions characterized by undesirable vascular smooth muscle cell proliferation, including vascular complications of diabetes. See, e.g., Harrisons, Principles of Internal Medicine (McGraw Hill, Inc., New York) for a more detailed description of these conditions. The method for treating an arteriosclerotic condition may be a surgical method, an agent for treating restenosis, a method involving a drug therapy (e.g., gene therapy) or a combination of the foregoing.

Surgical methods for treating an arteriosclerotic condition include procedures such as bypass surgery, atherectomy, laser procedures, ultrasonic procedures, and balloon angioplasty. In a preferred embodiment of the invention, the isolated GATA-6 molecule is administered to a subject in combination with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the arterial wall. As a result, the layer of endothelial cells on the surface of the artery is disrupted, thereby exposing the underlying vascular smooth muscle cells. The isolated GATA-6 molecule is attached to the balloon angioplasty catheter in a manner which permits release of the isolated GATA-6 molecule at the site of the atherosclerotic plaque. The isolated GATA-6 molecule may be attached to the balloon angioplasty catheter in accordance with standard procedures known in the art. For example, the isolated GATA-6 molecule may be stored in a compartment of the balloon angioplasty catheter until the balloon is inflated, at which point it is released into the local environment. Alteratively, the isolated GATA-6 molecule may be impregnated on the balloon surface, such that it contacts the cells of the arterial wall as the balloon is inflated. The GATA-6 molecule also may be delivered in a perforated balloon catheter such as those disclosed in Flugelman, et al., Circulation, v. 85, p. 1110–1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid to the balloon angioplasty catheter.

Additionally, the GATA-6 molecule may be administered with an agent for treating or preventing clinically significant restenosis, which often occurs following balloon angioplasty procedures. Restenosis is narrowing of the artery which occurs in 25% to 50% of patients within 6 months of an angioplasty procedure. Although restentosis was originally believed to be due completely to local tissue growth, recent findings have suggested that it may be due to a combination of tissue growth and vascular remodeling.

A preferred agent for preventing restenosis, in combination with the GATA-6 molecule, is a stent. Stents are discussed in a review article by Topol, E. J., the contents of which are hereby incorporated by reference (Topol, E. J., N. E. J. Med. 331:539–41 (1994)). Stents include, for example, the Gianturco-Roubin stent and the Palmaz-Schatz stent.

The arteriosclerotic conditions also can be treated by a nonsurgical method such as a drug therapy. Many drugs have been used to treat various aspects of an arteriosclerotic condition. For example, drugs have been used to treat physiological events, such as hypertension and excessive cholesterol accumulation, which are believed to contribute to the formation of atherosclerotic plaques. Other drugs influence the site of injury by breaking up or reducing the size of atherosclerotic plaques, and/or increasing the strength of the arterial wall. The isolated GATA-6 molecule may be administered in conjunction with either or a combination of drugs which inhibit the physiological events contributing to arteriosclerosis or drugs which function directly to reduce the local site of injury associated with atherosclerosis.

Drug therapies which have been found to be useful in treating the physiological events contributing to the development of the atherosclerotic injury, include, but are not limited to, the following drugs: diuretics, antiadrenergic agents, vasodilators, calcium channel antagonists, angiotensin-converting enzyme (ACE) inhibitors, angiotensin II antagonists, and clot dissolvers.

Diuretics include thiazides, e.g., hydrochlorothiazide; loop acting diuretics, e.g., furosemide; potassium-sparing, e.g., spironolactone, triamterene, and amiloride.

Antiadrenergic agents include clonidine; guanabenz; guanfacine; methyldopa; trimethapajn; Rauwolfia alkaloids, e.g., reserpine; guanethidine; guanadrel; phentolamine; phenoxybenzamine; prazosin; terazosin; propranolol; metoprolol; nadolol; atenolol; timolol; timdolol; acebutolol; and labetalol.

Vazodilators include hydralazine; minoxidil; diazoxide; and nitroprusside.

Calcium channel antagonists include nisadipine; diltiazen; and verapamil.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin -(1–8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1–7 (1988)); 4, 5, 6, 7-tetrahydro-1H-imidazo [4, 5-c] pyridine-6-carboxylic acid and analog derivatives (U.S. Pat. No. 4,816,463); N2-tetrazole beta-glucuronide analogs (U.S. Pat. No. 5,085, 992); substituted pyrroles, pyrazoles, and tryazoles (U.S. Pat. No. 5,081,127); phenol and heterocyclic derivatives such as 1,3-imidazoles (U.S. Pat. No. 5,073,566); imidazofused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); A$_2$ agonists (Marion Merrill Dow) and certain non-peptide heterocycles (G.D.Searle and Company).

ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075, 451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063, 207, 5,036,054, 5,036,053, 5,034,512, and 4,894,437).

Drugs which are clot dissolvers include thrombolytic agents which have been used in the treatment of acute venous thromboembolism and pulmonary emboli and are well known in the art (e.g. see Hennekens et al, *J Am Coll Cardiol*; v. 25 (7 supp), p. 18S–22S (1995); Holmes, et al, *J Am Coll Cardiol*; v.25 (7 suppl), p. 10S–17S(1995)). Thrombolytic agents include, for example, direct acting agents such as streptokinase and urokinase, and second generation agents such as tissue plasminogen activator (tPA).

Drug therapies which influence the site of injury include any drug which contributes to the reduction of an atherosclerotic plaque or to the strengthening of the arterial wall in the local area of injury. Drugs which help to contribute to the reduction of the plaque include cytostatic molecules, cytotoxic molecules which are cytotoxic to smooth muscle cells, and antisense agents to cell cycle regulatory molecules. Other drugs which contribute to the strengthening of the arterial wall include drugs which promote endothelial cell proliferation and function, such as cytokines.

In an embodiment of the invention, the isolated GATA-6 molecule is administered to a subject in combination with a cytostatic molecule. The cytostatic molecule is an agent (e.g., a nucleic acid, a protein) that suppresses cell growth and/or proliferation. A preferred cytostatic molecule is one which inhibits the growth and/or proliferation of vascular smooth muscle cells and includes the growth arrest homeobox molecule (GAX). The GAX molecule is described in published PCT Application WO95/23161. Other cytostatic molecules that are active with respect to vascular smooth muscle cells include the retinoblastoma protein (pRB), and cyclic kinase inhibitors, such as p21 and NO donors (Mooradian et al., *J. Cardiovasc. Pharmacol.* 25:674–8 (1995)).

In another embodiment of the invention, the isolated GATA-6 molecule is administered to a subject in combination with a cytotoxic molecule. A cytotoxic molecule is an agent which is toxic to the cell, and includes, for example, the so-called "suicide" enzymes such as thymidine kinase (TK) and its "suicide" substrate, gangcyclovir, DAB389 EGF (Pickering et. al.,*J. Clin. Invest*. 91:724–9 (1993)), and allylamine (Hysmith et al., *Toxicology* 38:141–50 (1986)).

In another embodiment of the invention, the isolated GATA-6 molecule may be administered to a subject in combination with an antisense oligonucleotide that selectively hybridizes to cell cycle regulatory molecules, such as c-myb, cdc2, cdk2, PCNA, and c-myc under physiological conditions. Such antisense oligonucleotides can function as cytostatic or cytotoxic agent, depending upon the relative amounts of the antisense oligonucleotides that are delivered to the cell and the importance of the particularly targeted cell cycle regulatory molecule to cell growth, proliferation and survival.

Certain cytokines function to strengthen the arterial wall by promoting endothelial cell proliferation. Cytokines which promote endothelial cell proliferation include, but are not limited to the following: vascular endothelial growth factor (VEGF), basic fibroblast growth factor (bFGF), and acidic fibroblast growth factor (aFGF). Substances that stimulate the proliferation or migration of normal endothelial cells include factors which are associated with the vascularization of tumors and substances which inhibit angiogenesis. Such substances include transforming growth factor beta (TGFβ), tumor necrosis factor alpha (TNFα), human platelet factor 4 (PF4), and alpha interferon (αINF); factors which suppress cell migration, such as proteinase inhibitors, tissue inhibitors of metalloproteinase (TIMP-1 and TIMP-2); and other proteins such as protamine which has demonstrated angiostatic properties.

The above-described drug therapies are well known to those of ordinary skill in the art and are administered by modes know to those of skill in the art. The drug therapies are administered in amounts which are effective to achieve the physiological goals (to prevent or reduce the physiological consequences of atherosclerosis), in combination with the isolated GATA-6 molecule of the invention. Thus, it is contemplated that the drug therapies may be administered in amounts which are not capable of preventing or reducing the physiological consequences of atherosclerosis when the drug therapies are administered alone but which are capable of preventing or reducing the physiological consequences of atherosclerosis when administered in combination with the isolated GATA-6 molecules of the invention.

The isolated GATA-6 molecule may be administered alone or in combination with the above-described drug therapies as part of a pharmaceutical composition. Such a pharmaceutical composition may include the isolated GATA-6 molecule in combination with any standard physiologically and/or pharmaceutically acceptable carriers which are known in the art. The compositions should be sterile and contain a therapeutically effective amount of the isolated GATA-6 molecule in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The isolated GATA-6 molecule may be administered alone or in combination with the above-described drug therapies by any conventional route, including injection or by gradual infusion over time. The administration may, for example, be oral, intravenous, intraperitoneal, intramuscular, intra-cavity, subcutaneous, or transdermal. When using the isolated GATA-6 molecule of the invention, direct administration to the vessel injury site, such as by administration in conjunction with a balloon angioplasty catheter, is preferred.

Preparations for parenteral administration include sterile aqueous or non-aqueous solutions. suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In general, the GATA-6 nucleic acids can be administered to the subject (any mammalian recipient) using the same modes of administration that currently are used for gene therapy in humans (e.g., adenovirus-mediated gene therapy). Preferably, the GATA-6 nucleic acid (contained in, or associated with, an appropriate vector) is administered to the mammalian recipient by balloon angioplasty catheter (described above) or intra-vascular injection.

Another aspect of the invention includes a screening assay method for determining whether a putative therapeutic agent modulates vascular smooth muscle cell proliferation. The method involves determining the amount of a GATA-6 molecule in a proliferating "test" cell that has been contacted with the putative therapeutic agent to determine whether the putative therapeutic agent modulates cellular proliferation by up or down regulating the amount of the GATA-6 molecule. An increase in the amount of the GATA-6 molecule in the "test" cell indicates that the putative therapeutic agent inhibits cell (e.g. vascular smooth muscle cell or tumor cell) proliferation. Optionally, the level of GATA-6 may be measured in a cell of the same cell type as a negative control in the measurement of proliferation or the level of GATA-6 may be measured in a cell of the same cell type which has been treated with the GATA-6 molecule of SEQ. ID. No. 1 or 2 as a positive control in the measurement of proliferation. In one embodiment of the invention the method also involves the step of contacting the GATA-6 molecule with a detection reagent that selectively binds to the GATA-6 molecule to detect or measure the amount of the GATA-6 molecule in the "test" cell. The GATA-6 molecule may optionally be isolated from the vascular smooth muscle or other cell prior to contacting the isolated GATA-6 molecule with the detection reagent. When the GATA-6 molecule is a GATA-6 mRNA, the detection reagent can be a nucleic acid that selectively hybridizes to the GATA-6 mRNA. According to this embodiment, the "test" cell is contacted with the detection reagent under conditions that permit selective hybridization of the nucleic acid to the GATA-6 mRNA. The preferred nucleic acid for this embodiment is a nucleic acid sequence having SEQ. ID. No. 1 or a unique fragment thereof. Alternatively, the GATA-6 molecule that is being assayed can be a GATA-6 protein and the detection reagent can be an antibody that selectively binds to the GATA-6 protein. The GATA-6 protein can be contacted with the detection reagent under conditions that permit selective binding of the GATA-6 antibody to the GATA-6 protein.

In another aspect, the invention includes a kit for determining if a vascular smooth muscle cell is undergoing proliferation. The kit may be in one or more containers and, preferably, includes any of the above-noted detection reagents. Optionally, the kit further includes a vehicle for facilitating the delivery of the detection agent into a vascular smooth muscle cell.

Each of the compositions of the invention is useful for a variety of purposes in addition to their uses as therapeutics in the methods of the invention. For example, the GATA-6 nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual*, 2nd ed., Cold Spring Harbor Laboratory Press, Plainview, N.Y. (1989), and by Hames, B. D., et al., in *Nucleic Acid Hybridization, A Practical Approach*, IRL Press, Washington, D.C. (1985). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, most any label useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci.* (*USA*) 80:4045 (1983); Renz, M. et al., *Nucl. Acids Res.* 12:3435 (1984); and Renz, M., *EMBO J.* 6:817 (1983).

Additionally, complements of the GATA-6 nucleic acids can be useful as anti-sense oligonucleotides, e.g., by delivering the anti-sense oligonucleotide to an animal to induce a GATA-6 "knockout" phenotype. The administration of anti-sense RNA probes to block gene expression is discussed in Lichtenstein, C., *Nature* 333:801–802 (1988).

Alternatively, the GATA-6 nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of GATA-6 knockout and transgenic animals as models for the study of disorders of vascular blood vessels, such as arteriosclerosis as well as for the study of abnormal cell proliferation associated with tumor growth and metastasis.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82:4438 (1985); Brinster et al., cell 27:223 (1981); Costantini et al., *Nature* 294:982 (1981); Harpers et al., *Nature* 293:540 (1981); Wagner et al., *Proc. Nat. Acad. Sci. USA* 78:5016 (1981); Gordon et al., *Proc. Nat. Acad. Sci. USA* 73:1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., *Molec. Cell Biol.* 7:1276 (1987); Lacey et al., *Nature* 322:609 (1986); Leopol et al., *Cell* 51:885 (1987). Embryos can be infected with viruses, especially retroviruses, modified to carry the nucleotide sequences of the invention which encode GATA-6 proteins or sequences which disrupt the native GATA-6 gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., *Cold Spring Harbor Conference Cell Proliferation* 10:647 (1983); Bradley et al., *Nature* 309:255 (1984); Wagner et al., *Cold Spring Harbor Symposium Quantitative Biology* 50:691 (1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47:897–905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell*, 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination (Capecchi, *Science*, 244:1288–1292 (1989)). Methods for positive selection of the recombination event (e.g., neo resistance) and dual positive-negative selection (e.g., neo resistance and gang-cyclovir resistance) and the subsequent identification of the desired clones by PCR have been described by Capecchi, supra and Joyner et al., *Nature*, 338:153–156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., *Science* 244: 1281–1288 (1989); and Simms et al., *BioTechnology*, 6:179–183 (1988).

Inactivation or replacement of the endogenous GATA-6 gene can be achieved by a homologous recombination system using embryonic stem cells. The resultant transgenic non-human mammals having a knockout GATA-6 characteristic may be used as a model for atherosclerosis. Vascular smooth muscle cells which do not express GATA-6 may be predisposed to proliferate and thus, produce an atherosclerotic phenotype. A variety of therapeutic drugs can be administered to the phenotypically atherosclerotic animals to determine the affect of the therapeutic drugs on vascular smooth muscle cell proliferation. In this manner, therapeutic drugs which are useful for preventing or reducing vascular smooth muscle cell proliferation can be identified. Such agents are useful for, e.g., treating atherosclerosis.

Additionally, a normal or mutant version of GATA-6 can be inserted into the mouse germ line to produce transgenic animals which constitutively or inducible express the normal or mutant form of GATA-6. These animals are useful in studies to define the role and function of GATA-6 in cells.

The invention will be more fully understood by reference to the following examples. These examples, however, are merely intended to illustrate the embodiments of the invention and are not to be construed to limit the scope of the invention.

EXAMPLES

Example 1

Identification, Structural Analysis and tissue distribution of the human GATA-6 gene Methods:

Isolation and sequencing of luman GATA-6 cDNA clones. Human GATA-6 cDNA was isolated by either of the two following methods.

Several GATA-6 clones were isolated from a λgt11 human fetal heart cDNA library (from Leonard Zon) and sequenced by standard methods commonly used in the art. The library was screened using standard hybridization conditions (Sambrook, et al., *Molecular Cloning, A Laboratory Manual*, 2nd ed., Cold Spring Harbor Laboratory Press, Plainview, N.Y. (1989)) at 50° C. with a probe mixture consisting of a Xenopus GATA5a (Kelley et al., *Development*, 118:817–827 (1993)) and a chicken GATA-4 (Laverriere et al., *J. Biol. Chem.* 269:23177–23184 (1994)) cDNA. Inserts from several positive clones were isolated and amplified by PCR and subcloned into the pCRII™ vector (Invitrogen). DNA from the phages was purified and the GATA-6 encoding insert was subcloned in pBluescript SkII-(Stratagene) and sequenced. An adult human heart cDNA library in the lambda ZAPII vector (Stratagene), was screened with the GATA-6 DNA sequence isolated from the λgt11 human fetal heart cDNA library. A 1.6 kb insert from a single positive plaque was isolated and sequenced. This sequence was found to contain a sequence identical to the clone derived from fetal RNA.

Alternatively, GATA-factor cDNAs were also isolated from vascular smooth muscle cells. Degenerate PCR primers were designed within the zinc-finger domains such that all isoforms of GATA-binding transcription factors could potentially be amplified. The DNA templates for PCR amplification were either extracted from a human aorta λgt11 phage library (Clontech) or were reverse transcribed RNA that was extracted from cultured human vascular smooth muscle cells. One µg of total RNA was processed by reverse transcriptase reaction according to the directions of the manufacturer (Perkin-Elmer). The primer sequences for PCR were as follows:

Sense: 5'-GA(A/G)GCI(A/C)GIGA(A/G)TG(C/T)GTIAA(C/T)TG-3' (SEQ. ID. No. 3)
Antisense 5'-(A/G)TAIA(A/G)ICC(A/G)CAIGC(A/G)TT(A/G)CAIAC-3' (SEQ. ID. No. 4)
wherein I=deoxyinosine.

PCR was performed in 50 ml of reaction volume containing 2 mM $MgCl_2$, 50 mM KCl, 10 mM Tris-HCl (pH 8.3), 0.2 mM deoxyribonucleotide triphosphate mixture, 1 mM sense and antisense primers and 1 unit of Taq DNA polymerase (Perkin-Elmer). The amplification conditions were 95° C.; 1 min, 72° C.; 1 min for 40 cycles. Total RNA was isolated from human vascular smooth muscle cell cultures by acid guanidinium thiocyanate-phenol-chloroform extraction method (Chomczynski and Sacchi, *Anal. Biochem.* 162:156–159 (1987)). PCR amplified products were directly subcloned into the pCRII™ vector (Invitrogen) for subsequent sequence analysis.

Sequence analysis of each DNA sample was determined by the cycle sequencing method using fluorescent dideoxy terminator nucleotides with an Applied Biosystems 373A Automated DNA sequencer.

RNA Analysis. The tissue distribution of GATA-6 was determined by Northern Blot analysis or Quantitative Reverse Transcription-Polymerase Chain Reaction (RT-PCR). RNA samples were obtained as Poly A RNA from various human tissues (which was purchased from Clontech) and prepared for analysis. Northern blot analysis was performed by standard techniques well known in the art. RT-PCR was performed by procedures known in the art. Briefly, PCR was performed in 25 µl of reaction volume containing 2 mM $MgCl_2$, 50 mM KCl, 10 mM Tris-HCl (pH 8.3), 0.2 mM deoxyribonucleotide triphosphate mixture, 1 mM sense and antisense primers, 5 mCi of $\alpha$-$^{32}$P dCTP, and 0.5 unit of Taq DNA polymerase. G3PDH transcript was amplified as an internal standard. The amplification condition was 95° C.; 1 min, 55° C.; 1 min, 72° C.; 1 min for 20 cycles for G3PDH, and 25 cycles for rat GATA-6. The PCR amplified products were analyzed by 6% nondenaturing polyacrylamide gels. The primers were designed to be specific for the GATA-6 isoform. The sequences of the primers were as follows:

Sense 5'-CGTGAACTGTGGCTCCATCCA-3' (SEQ. ID. No. 5)
Antisense 5'-AGTTGGCACAGGACAGTCCAA-3' (SEQ. ID. No. 6)

Results:

1. Identification of tile Structural Domains of the human GATA-6 gene

A GATA-6 gene was isolated (as described in the methods) and several structural domains were identified. The GATA-6 cDNA has an open reading frame from nucleotide residue 348 to nucleotide residue 1,697 (SEQ. ID. No. 1). One can predict that the GATA-6 protein is 45.3-kda and is comprised of 449 amino acids based on the size of the open reading frame (SEQ. ID. No. 2). The predicted GATA-6 protein contains two zinc-finger domains similar to those found in other members of the GATA-binding transcription factor family followed by a highly conserved region which contains a high frequency of basic amino acids. The region between the zinc fingers is also highly conserved and contains abundant basic residues. The human GATA-6 gene also contains a GCX trinucleotide repeat which encodes 11 consecutive alanine residues and a CAX trinucleotide repeat which encodes 10 consecutive histidine residues.

The chromosomal location of the human GATA-6 gene was also determined by Fluorescent in situ hybridization (FISH) mapping. Normal human metaphase spreads were prepared according to the method of Fan (Fan et al., *Proc. Natl. Sci. USA* 87:6223–6227 (1990)). A 1.5-kb fragment of the 3'UTR of GATA-6 was used as a hybridization probe. FISH mapping was performed as previously described (Testa et al., *Cytogenet. Cell Genet.* 60:247–249 (1992)). Hybridization of the probe from the 3'UTR of GATA-6 to human chromosomes showed specific labeling on chromosome 18.

2. Tissue Distribution of GATA-6 expression in human tissues

Northern blot analyses were performed to determine the distribution of GATA-6 transcripts in human tissues. In embryonic tissue, GATA-6 transcripts were expressed at exceptionally high levels in the heart and at moderately high levels in the lung. Little or no expression was detected in brain, liver or kidney. In adult, GATA-6 transcripts were expressed at high levels in heart, ovary, lung, and pancreas. Lower levels of expression were detected in adult liver and spleen, and little or no expression was detected in brain, placenta, skeletal muscle, thymus, prostate, testes, small intestine, colon, or leukocytes.

Example 2

Regulation of GATA-6 expression in vascular smooth muscle cells corresponds to the Proliferative State of the Cell Methods:

Cell culture. Internal mammary artery or saphenous vein was the source of cultured human vascular smooth muscle cells prepared by the explant method (Ross, *J. Cell Biol.* 50:172–186 (1971)). In brief, adventitia and endothelium were removed by scraping with a scalpel, and the vessels were cut into small pieces with a blade. The fragments were placed on a 60 mm culture dish with adventitia side up, and incubated at 37° C. in Dulbecco's modified Eagle medium (DMEM) containing 15% fetal bovine serum (FBS) for one week. The vascular smooth muscle cells migrating from the fragments were trypsinized and subcultured in DMEM containing 10% FBS (high serum medium). When cultured cells reached 50–60% confluence, the medium was replaced with low serum medium, DMEM with 0.5% FBS, and the cells were incubated at 37° C. for 3–4 days in a humidified incubator to induce quiescence. Primary cultures of rat smooth muscle cells were prepared from thoracic aortas of adult male Sprague-Dawley rats according to Mader (Mader et al., *J Gerontol. Biol. Sci.* 47:B32–36 (1992)). COS1 cells were cultured in DMEM with 10% FBS.

RNA analysis of GATA-6 expression in vascular smooth muscle cells. RNA from a series of clones from a human vascular library was amplified by PCR of GATA transcription factors (GATA-1 through GATA-6) using degenerate primers corresponding to highly conserved zinc finger domains (SEQ. ID. No. 3 and 4) of each transcription factor. Each PCR product was sequenced by the cycle sequencing method using fluorescent dideoxy terminator nucleotides with an Applied Biosystems 373A Automated DNA sequencer. Total RNA was also analyzed by Northern Blot Analysis (as described above).

Results:

DNA Sequence analysis of the 20 independent DNA samples obtained by PCR revealed that all 20 encoded the GATA-6 isoform. These results suggest that GATA-6 is the predominant isoform expressed in vascular smooth muscle cells.

Northern blot analyses (as described above) were performed to further examine GATA-6 expression in vascular smooth muscle cells. A single GATA-6 transcript was observed by Northern blot analysis in both human and rat vascular smooth muscle cells that had been made quiescent by serum deprivation for 3 days. GATA-4 expression was not detected in human or rat vascular smooth muscle cells by Northern blot analysis even when the membranes were exposed to film for prolonged periods of time.

Stimulation of quiescent human vascular smooth muscle cultures with 10% fetal bovine serum resulted in a striking decrease in GATA-6 mRNA levels by 1 hour. Maximal downregulation appeared to occur by 4 hours and reduced expression was maintained for 24 hours. At later time points (48 hours) GATA-6 expression returned to its prestimulation levels. In rat vascular smooth muscle cells, the regulation of GATA-6 expression by mitogens appeared more complex. In these cultures maximal GATA-6 downregulation occurred by 4 hours, following a transient upregulation at 0.5 and 1 hrs. after serum stimulation. Furthermore, GATA-6 transcript levels returned to their pre-stimulation levels by 16 hours, much sooner than in the cultures of the human vascular smooth muscle cells. Due to the complexity of the GATA-6 expression in the serum-stimulated rat vascular smooth muscle cells, GATA-6 downregulation was independently assessed in these cultures by reverse transcription/PCR amplification under quantitative conditions using GATA-6-specific primers. In this analysis glyceraldehyde 3-phosphate dehydrogenase (G3PDH) transcripts were co-amplified as an internal control. The ratio of rat GATA-6 to G3PDH transcript levels decreased by 4-fold at the 4 hour time point (0 hr; 0.36±0.05 vs. 4 hr; 0.09±0.01) which appeared to be the nadir of expression based upon Northern blot analysis. Collectively, these results show that GATA-6 expression is rapidly decreased early in the G1 phase of the cell cycle when vascular smooth muscle cells are induced to proliferate by mitogen stimulation.

A striking feature of GATA-6 expression in vascular smooth muscle cells is its rapid downregulation following mitogen activation. Expression of GATA-6 was transiently reduced within hours of mitogen stimulation in both human and rat vascular smooth muscle cells, albeit with different kinetics. The pattern of GATA-6 expression is similar to that described for the gas (growth arrest-specific) and gadd (growth arrest and DNA damage inducible) families of genes that are rapidly downregulated in response to proliferative signals and more slowly upregulated under conditions that lead to growth arrest (Fornace et al., *Mol. Cell. Biol.* 9:4196–4203 (1989); Schneider et al., *Cell* 54:787–93 (1988)). Notably, a number of gas and gadd genes have been found to encode for proteins that arrest cell growth (Barone et al., *Genes Dev.* 8:453–464 (1994); Del Sal et al., *Cell* 70:595–607 (1992); Zhan et al., *Mol. Cell. Biol.* 14:2361–2371 (1994)). Previous studies have identified genes in vascular smooth muscle cells with expression properties similar to that of the gas and gadd gene families. Expression of the gax homeobox gene is downregulated in quiescent cultures of vascular smooth muscle cells by mitogen stimulation (Gorski et al., *Mol. Cell. Biol.* 13:3722–3733 (1993); Gorski et al., *Trends Cardiovasc. Med.* 3:184–190 (1993)) and its expression is also downregulated in rat carotid arteries following vascular injury (Weir et al., *J. Biol. Chem*; 270:5457–5461 (1995)). Similarly, the zinc finger protein SmLIM, is downregulated following mitogen activation in cultured vascular smooth muscle cells and after balloon injury in rat carotid arteries (Jain et al., *J Biol Chem.* 271:10194–10199 (1996)).

Mitogen regulated transcription factors reportedly may mediate changes in the vascular smooth muscle phenotype in response to growth factor stimulation (Gorski et al., *Cardiov. Res.* 30:585–592 (1995)). Unlike cardiac and skeletal smooth muscle cells, vascular smooth muscle cells do not terminally differentiate and can reversibly modulate their phenotype and cell cycle activity in response to growth factor stimulation (Campbell, *Ann. NY Acad. Sci.* 598:143–158 (1990); Campbell, *In Vascular Smooth Muscle in Culture* (ed.) p. 39–55, CRC Press, Inc., Boca Raton (1987)). Differentiated "contractile" vascular smooth muscle cells are quiescent and express high levels of contractile protein isoforms. On the other hand, mitogen stimulation promotes the "synthetic" vascular smooth muscle phenotype and these types of cells are thought to occur in proliferative vessel wall lesions. Synthetic cells express lower levels of contractile proteins and generally appear to resemble their fibroblast-like precursor cells. Therefore, GATA-6 may function to coordinate the expression of vascular smooth muscle genes with cell cycle progression during the initial phases of phenotypic modulation. Genes expressed in vascular smooth muscle cells that may be regulated by GATA-6 include elastin, Pal-1, VCAM1, and vimentin because conserved GATA binding sites occur within their promoters. Alternatively, the level of GATA-6 expression may modulate vascular smooth muscle cell cycle activity by modulating the expression of cell cycle regulatory proteins.

Example 3

GATA-6 Reversibly Growth Arrests Vascular Smooth Muscle Cells

Methods:

Proliferation Assay in A7r5 cells. A7r5 cells were transiently transfected with the test plasmid (an expression plasmid for GATA-6 (pGATA-6), Gax (pCGN-Gax) or a control plasmid (pCDNA)) and with pMSVβ-gal reporter construct plasmid that expresses the β-galactosidase gene using a procedure that was described previously (Simonson, M. S.et al., *BioTechniques* 18:434–442(1995)). Twenty-four hours after transfection, cellular DNA was labeled for 24 hours with BrdU (5-bromo-2-deoxyuridine) in accordance with standard procedures. Cultures were then fixed using standard procedures and transfected cells were identified with an immunohistochemical stain for β-galactosidase (6-chloro-3-indolyl-β-D-galactopyranoside). Transfected cells (positive for staining with 6-chloro-3-indolyl-β-D-galactopyranoside) that transversed S phase were quantified by immunohistochemical staining for BrdU.

ProliferationAssay in 10(1) moise embryofibroblasts (p53-/-). 10(1) mouse embryo fibroblasts (p53-/-) were plated on gelatin and placed in low serum media for 3 days. Cells were transfected with the test expression plasmids pCGN-GATA-6 or pCGN-Gax that encode proteins fused to the hemagglutinin (HA) epitope for antibody tagging purposes. Following the transfection procedure, cells were exposed to growth medium (with 10% fetal bovine serum) for 24 hours, then BrdU was added to the media for an additional 24 hours. Cells were then fixed and permeabilized. Transfection-positive cells were identified with a mouse anti-HA primary antibody and a donkey anti-mouse secondary antibody coupled to rhodamine. BrdU-positive cells were detected with a mouse anti-BrdU antibody coupled to FITC.

Results:

The growth regulatory properties of GATA-6 were analyzed in the vascular smooth muscle cell line A7r5 and in 10(1) mouse embryo fibroblasts that are null for the p53 gene. In both cell types the growth arrest was analyzed by transient co-transfection assays, and the effect of GATA-6 overexpression was compared with that of the homeobox gene Gax, a known negative regulator of cell growth.

The results of 2 independent experiments performed in duplicate on the vascular smooth muscle cell line A7r5 are presented in Table 1. pGATA-6 inhibited DNA synthesis (growth) by 60% relative to control, while pCGN-Gax inhibited growth by 42%. Chi square analysis revealed significant growth inhibition by GATA-6 relative to the control (p<0.01).

TABLE 1

Inhibition of growth in transiently transfected A7r5 cells

| Condition | n | Cells with BrdU⁺ nuclei | Growth inhibition |
|---|---|---|---|
| pCDNA (control) | 281 | 78% | — |
| pGATA-6 | 397 | 31% | 60% |
| pCGN-Gax | 343 | 45% | 42% |

Transfected (vs. non-transfected) 10(1) mouse embryo fibroblasts (p53-/-) were scored for their ability to incorporate BrdU by immunofluorescence (Table 2). Approximately 100 HA-positive or non-transfected cells were analyzed. Under the conditions of this assay >99% of the non-transfected cells incorporated BrdU (i.e. traversed S phase within the 24 hour labeling period). Only 25% of cells transfected with pCGN-GATA-6 and 49% of cells transfected with pCGN-Gax transversed S phase under these conditions. The extent of growth inhibition by overexpression of GATA-6 was 75% and by overexpression of Gax was 51%.

TABLE 2

Inhibition of growth in transiently transfected 10(1) mouse embryo fibroblasts

| Condition | Cells with BrdU⁺ nuclei | Growth inhibition |
|---|---|---|
| nontransfected | >99% | — |
| pCGN-GATA-6 | 25% | 75% |
| pCGN-Gax | 49% | 51% |

In an identical experiment, 10(1) mouse embryo fibroblasts were transfected with the same GATA-6 expression vectors and labeled with BrdU. Double immunofluorescence to detect BrdU and GATA-6 co-localization at 24 hours post-transfection revealed that GATA-6 inhibited S-phase entry by 95+/-1% (using an anti-GATA-6 antibody as prepared in Example 7, instead of an-anti-HA antibody). Similar results were obtained when GATA-6 transfected cultures were assessed at 48 hours, indicating that GATA-6 blocks, rather than delays, S-phase entry.

Example 4

In Vitro Assay for Selecting GATA-6 Molecules that Modulate Vascular Smooth Muscle Cell Proliferation In order to determine whether a particular molecule is a functionally active GATA-6 molecule of the invention, an in vitro assay for detecting proliferation of vascular smooth muscle cells is performed. A putative GATA-6 molecule (i.e., a molecule being tested for GATA-6 activity) and, optionally, a GATA-6 molecule control (i.e., a GATA-6 molecule having known vascular smooth muscle cell proliferation inhibitory activity) are administered to proliferating populations of cultured vascular smooth muscle cells, such as A7r5 cells. The cultured cells are maintained in media containing the test molecule for up to 72 hours. At various time points the cells are harvested and the proliferative state is determined by an immunohistochemical assay. Immunohistochemical assays which are useful in measuring proliferation in vascular smooth muscle cells include a BrdU assay and a proliferating cell nuclear antigen (PCNA) assay. The BrdU assay is performed as described above in Example 3. The PCNA assay is described in many references including More et al., *J. Path* 172:287–292 (1994) which is hereby incorporated by reference. Briefly, the cells are fixed onto the tissue culture dish and dried over night at 37° C. and immunostained using a monoclonal antibody to PCNA, such as PC10 (Dakopatts, Denmark) or anti-PCNA 19F4. The immunostained sections are examined by light microscopy. The immunostained cells are counted and the quantity of proliferating cells may be expressed as the percentage of PCNA immunostained cells to the total number of cells examined. PCNA expression may also be assayed by immunoblot or immunoflorescence as described in Johnson and Allen, *J Cell Physiol* 154:39–43 (1993).

A putative GATA-6 molecule that inhibits vascular smooth muscle cell proliferation in the above assays is a functionally active GATA-6 molecule of the invention. Such a high throughput assay can be used by those of ordinary skill in the art to identify functionally equivalent GATA-6 molecules using no more that routine experimentation. By substituting a different proliferating cell type for vascular smooth muscle cells, the above described procedure also can be used to select GATA-6 molecules that modulate other cell, e.g. tumor cell, proliferation. For example, tumor cells obtained by biopsy and cultured can be used in place of vascular smooth muscle cells to identify GATA-6 molecules that inhibit tumor cell proliferation in vivo and in vitro. Thus, the in vitro assay disclosed herein is predictive of the in vivo action of a GATA-6 molecule with respect to mediating cell proliferation.

Example 5

In Vivo Models for the Regulation of Vascular Smooth Muscle Cell Proliferation by GATA-6

Several in vivo animal models of vascular disorders exhibiting excessive smooth muscle cell proliferation are currently being used to study the efficacy of drugs in inhibiting vascular smooth muscle cell proliferation. The models include a rabbit model of balloon angioplasty (More et al., *J. Path* 172:287–292 (1994)), hypercholesterolemia-induced atherosclerosis in a nonhuman primate (Chang et al., *Arterioscler Thromb Vasc Biol* 15:1631–40 (1995)), a rat model of balloon angioplasty (Zeymer et al., *Am. J Pathol.* 141:685–90 (1992)) and a porcine proliferative restenosis model (Carter et al., *J Am. Coil. Cardiol* 24:1398–405 (1994)). The rabbit model is a well established model and is preferred for the GATA-6 studies. A brief description of an experiment for determining the ability of a putative GATA-6 molecule to inhibit cellular proliferation in the rabbit model is provided below.

New Zealand White rabbits are subjected to a balloon angioplasty procedure to introduce an injury to the vascular wall. The rabbits are anesthetized and administered heparin intravenously (100 U/kg via an ear vein) just prior to the angioplasty procedure. An arteriotomy is made in a major artery followed by the introduction of an angioplasty balloon into the artery. At an appropriate site the balloon is inflated repeatedly several times to cause local injury to the artery wall. The balloon is then removed and the arteriotomy site is tied off proximally.

The rabbits are treated with either the putative GATA-6 molecule or a control GATA-6 molecule. Although the putative GATA-6 and control GATA-6 molecules may be administered by any of the methods described above in the detailed description of the invention, the molecules are preferably administered by release from the balloon angioplasty catheter, i.e., the balloon angioplasty catheter is constructed and arranged to release the GATA-6 molecule from a compartment or from its surface following inflation such that the molecules are released into the injured artery wall when the balloon is inflated.

The changes in vascular smooth muscle cell proliferation are observed at 30 min, 2 hrs, 12 day, 3 days, 7 days, 14 days, 1 month, and 3 months after the arterial wall injury. Animals are sacrificed and the arterial wall is removed. The arterial wall may then be fixed and subjected to immunohistochemistry procedures as described above in Examples 3 and 4.

A decrease in vascular smooth muscle cell proliferation as a function of administration of the putative GATA-6 molecule means that the putative GATA-6 molecule has GATA-6 activity and is a functionally equivalent GATA-6 molecule of the invention. The ability of the GATA-6 molecules of the invention to inhibit vascular smooth muscle cell proliferation in vivo demonstrates the ability of the molecule to be useful in the treatment of vascular disorders. By substituting a different animal model of disease for the animal model of vascular disorders, the above described procedure also can be used to select GATA-6 molecules that are useful in treating other diseases associated with excessive cellular proliferation, such as cancer.

Example 6

Identification of Functional GATA-6 Domains

Domain-swapping experiments between GATA-6 and other well characterized GATA factors (e.g., human GATA-4 and human GATA-5), or other well known transcription factors may be performed in order to determine the functional roles of each domain. In these experiments, plasmid expression vectors are constructed by routine techniques from fragments of the GATA-6 sequence and fragments of the above-described genes which are ligated by DNA ligase such that a fusion protein containing the respective portions of these two proteins will be synthesized by a whole cell transfected with the plasmid. The fusion protein having at least one GATA-6 domain can be substituted for the GATA-6 molecule in any of the above described proliferation assays to determine whether the at least one region of GATA-6 maintains the function of GATA-6. Exemplary swapping experiments are described in PCT Application No. PCT/US95/05518 filed on May 3, 1995, entitled Methods and Compositions for Modulating Heterotypic E-cadherin Interactions with T Lymphocytes having publication No. WO95/29693.

Example 7

Deletion of the zinc finger domain renders GATA-6 nonfunctional

Methods:

Cell culture. Cells were incubated at 37° C. in Dulbecco's modified Eagle medium (DMEM) containing 10% fetal bovine serum (FBS) and penicillin/streptomycin. Primary cultures of rat smooth muscle cells were prepared from thoracic aortas of adult male Sprague Dawley rats according to Mader (*J. Gerontol. Biol. Sci.* 47:B32–B36 (1992)). COS1 cells were cultured in DMEM with 10% FBS. Mouse embryonic fibroblasts with a homozygous deletion of the p53 allele designated p53−/− MEFs were a generous gift from Dr. Arnold Levine (Harvey et al., *Genes & Dev.*, 5:2375–2385 (1991)). Mouse embryonic fibroblasts that contain a homozygous disruption of the p21 allele (p21−/− MEFs) were a generous gift from Dr. Philip Leder (Deng et al., *Cell*, 82:675–684 (1995)). P53−/− MEFs were induced to the quiescent state by serum starvation for 3 days in 0.5% FBS DMEM while p21−/− MEFs cells were serum starved in 0.2% FBS DMEM for 4 days.

Plasmids and COS1 Transfections. Human GATA-6 wild type cDNA that was originally subcloned into pBluescript vector (pBS-hGATA-6wt) was subcloned into pCDNA1/Amp vector (Invitrogen) at Hind III and XbaI sites (pCDNA1-hGATA-6wt). The zinc-finger domains deletion mutant, which lacked codons 244 to 306 of SEQ. ID. No. 2, was prepared by digesting pBS-hGATA-6wt with EcoRi and PflmI and ligating a double-strand oligonucleotide (ΔZF1: sense strand-SEQ. ID. No. 7, ΔZF2: anti-sense strand-SEQ. ID. No. 8). The insert was subcloned into pCDNA1/Amp vector at HindIII and XbaI sites (PCDNA1-hGATA-6ΔZFΔ244-306).

Oligonucleotide sequences were as follows:

AZF1  5'TGGAGGACCTGTCCGAGAGCCGCGAGACCTT-3' (SEQ. ID. No. 7)

AZF2  5'GTCTCGCGGCTCTCGGACAGGTCCTCC-3'    (SEQ. ID. No. 8)

15 µg of each construct was transiently transfected in COS1 cells by the calcium phosphate method. The cells were harvested 48 hours after transfection and whole cell extracts were prepared. The p21 cDNA was subcloned into pCDNA1/Amp expression vector and was used as a positive control for the cell cycle inhibition experiments.

The rat Gax open reading frame was obtained by PCR amplification of a plasmid derived from λ ZAP cDNA clone as previously described (Smith et al., Genes & Dev., 11:1674–1689 (1997)). The fragment was inserted into the pCGN vector that contains the N-terminal part of the influenza virus hemagglutinin (HA).

Electrophoretic mobility shift assay. Whole-cell extracts were prepared from COS1 cells. In brief, cells were washed twice in PBS, removed from culture dishes by scraping and collected by centrifugation. The pellet was resuspended in an equal volume of 2× lysis buffer (2 mM HEPES-KOH (pH 7.8), 0.6 M KCl, 1 mM dithiothreitol, 20% glycerol, 2 mM EDTA, 2 µg/ml leupeptin and subjected to three cycles of freezing and thawing. After centrifugation at 16,000 g for 10 minutes at 4° C., the supernatant was stored at −80° C. Protein concentration was measured by the Bradford method according to the direction of the manufacturer (Bio-Rad). Electrophoretic mobility shift assays were carried out in reaction mixtures containing 5–20 µg of extract, 20 fmol of probe, 1 µg of poly (dI-dC), and 200 ng of single-stranded oligonucleotide as nonspecific DNA competitors. Electrophoresis was carried out on 5% non-denaturing polyacrylamide gels with 0.5×TBE (45 mM tris [hydroxymethyl] aminomethane, 45 mM boric acid, 1 mM EDTA) in a circulating water-cooled gel box. A probe to GATA site was prepared from the mouse globin gene. Probes and competitor DNAs were double stranded synthetic oligonucleotides, and the coding-strand sequences were as follows:

immunoglobin/ml, 1:100 dilution) or anti-human α-smooth muscle actin antibody (DAKO, 1:200 dilution) for overnight at 4° C. in PBS/0.2% Tween 20/2% nonfat dry milk. Filters were washed in PBS/0.2% Tween 20/2% nonfat dry milk, and incubated with anti-rabbit or anti-mouse secondary antibody that was conjugated with horse radish peroxidase (Amersham). Visualization of the immuno-complexes were carried out as recommended by the manufacturer (Enhanced Chemiluminescence kit; Amersham).

Results:

We compared the functionality of two plasmid constructs that express either wild-type GATA-6 or a mutant GATA-6 that lacks the conserved zinc finger binding domain, ΔZF-GATA-6. The wild-type and mutant GATA-6 proteins were comparably expressed in transfected COS1 cells as determined by Western blot analysis. The specificity of the anti-GATA-6 antibody was indicated by an abrogation of signal when the primary antibody was preabsorbed with a molar excess of immunogenic peptide. Nuclear extracts from transfected cells were incubated with a double stranded radiolabeled oligonucleotide corresponding to the consensus GATA site that occurs in the mouse globin gene and electrophoresed on a non-denaturing gel. Recombinant GATA-6 protein formed a nucleoprotein complex that was sensitive to competition by a molar excess of non-labeled wild-type probe, while a mutant oligonucleotide had no effect. In contrast to the wild-type protein, the ΔZF-GATA-6 was unable to bind to the radiolabeled oligonucleotide. Preincubation of rabbit anti-GATA-6 antibody with the nuclear extract induced a supershift band further demonstrating the specificity of the interaction. These expression vectors were further utilized to examine the growth regulatory properties of GATA-6.

GATA         5'-GCCGGGCAACTGATAAGGATTCCCA-3'  (SEQ. ID. No. 9)

GATA mutant 5'-GACCGGGCAACTGcgAAGGATTCCCA-3'  (SEQ. ID. No. 10)

Nucleotides in bold highlight the conserved protein binding motifs, and the lower case letters designate the mutated nucleotides. One pmol of the probes were 5'-terminally labeled with γ-$P^{32}$ ATP and used at a concentration of 10 fmol/µl.

Antibodies. Three different peptide sequences (amino acids 8–22, 373–387, 428–442, of SEQ. ID. No. 2) of human GATA-6 were used to raise antibodies against human GATA-6. These peptides were individually or conjugated to KLH, and injected in two New Zealand white rabbits subcutaneously. The immunoglobin fraction of the anti-sera was purified with protein A sepharose CL-4B according to the instructions of the manufacturer (Pharmacia-LKB). The purified anti-rabbit GATA-6 antibodies were used for Western blot analysis, immunoprecipitation and immunofluorescence.

Western Blot Analysis. Whole-cell extracts were prepared from COS1 cells. 50 µg of the extracts were applied to a 10% SDS-polyacrylamide gel, and transferred to Immobilon-P (Millipore) by semidry blotting. Filters were blocked for 1 hour at room temperature in phosphate-buffered saline (PBS)/0.2% Tween 20/5% nonfat dry milk. The filters were then incubated with anti-human GATA-6 antibody (1 mg Example 8

Ectopic GATA-6 expression induces p21 in p53-deficient cells

Methods:

Double Immunofluorescence. p53−/− MEFs were cultured on 60 mm plates containing 1.5% gelatin coated glass coverslips. Cells were serum starved for three days in 0.5% FBS DMEM. 5 µg of plasmid were transfected using the LipofectAmine procedure as described above. 24 hours after serum stimulation cultures were fixed in 4% neutral buffered formalin for 10 minutes. Cells were permeabilized for 5 minutes using 0.1% NP-40 and blocked in 2% goat serum. 2.5 µg/ml of mouse anti-p21 antibody were mixed with 1 µg/ml of rabbit anti-GATA-6 and incubated with the cells at 4° C. for overnight. Coverslips were washed and incubated with 1:200 dilution of FITC conjugated goat anti-mouse antibody and 1:800 dilution of goat anti-rabbit rhodamine conjugated antibody. Nuclei were counter stained with Hoechst 33258 and mounted on glass slides.

Results:

The p21 cdk inhibitor has been implicated in GI cell cycle arrest in GSMCs and other cell types (Chang et al., J. Clin.

Invest., 99:2334–2341 (1997), Smith et al., *Genes & Dev.*, 11:1674–1689 (1997)). Therefore, p21 expression was examined in the GATA-6 transduced cells. Double immunofluorescence assays revealed that non-transfected p53–/– MEFs do not express detectable levels of –21, presumably due the lack of –53 activation of the p21 promoter (El-Deiry et al., *Cell*, 75:817–825 (1993)), but an intense p21 signal was detected in cells that were positive for wild-type GATA-6 expression. Analysis of more than 100 transfected cells revealed robust expression of p21 in every GATA-6-positive cell. In contrast, no detectable p21 expression was found in any of the more than 100 ΔZF-GATA-6-positive cells that were examined. Therefore, the GATA-6 dependent inhibition of cell cycle activity was correlated with the upregulation of p21.

Example 9

GATA-6 transactivates the p21 promoter

Methods:

Transactivation of tlze p21 promoter. pGL2-WWP(2.5 Kb) was constructed by subcloning the HindIII/HindIII fragment of p21 promoter from the WWP-Luc construct into HindIII site of pGL2/Basic plasmid, and the orientation of the fragment was confirmed by DNA sequencing. pGL2-WWP(2.4 Kb) was derived from pGL2-WWP(2.5 Kb) by deleting SacI fragment and re-litigation. 1.4 Kb and 0.6 Kb fragments were PCR amplified from the p21 genomic DNA and subcloned into the KpnI/SacI sites of pGL2-WWP(2.4 Kb), thereby generating the p21-3.8 and p21-3.2 promoter constructs, respectively. Sub-confluent p53–/– MEFs were plated in 6 well plates and induced into quiescence by incubation for 3 days in 0.5% FBS DMEM. For transient transfections, 0.5 µg reporter plasmid was mixed with 2 µg of the wild-type GATA-6 or ΔZF-GATA-6 expression vectors. In each transfection, 0.5 µg of pSV2-AP plasmid was included to adjust for differences in transfection efficiency. This plasmid has the alkaline phosphatase reporter gene under the control of SV40 promoter. DNA mixtures were incubated with LipofectAmine (Gibco BRL) (DNA:LipofectAmine=1:6) at room temperature for 40 mintues. DNA/LipofectAmine mixtures were incubated with cells for 4 hours, after which cells were switched to DMEM medium supplemented with 0.5% FBS. 40 hours post-transfection, cells were lysed with 1× lysis buffer (Promega). Extracts were heat-treated for 25 minutes at 65° C. Alkaline phosphatase activity was measured using CSPD chemiluminescent substrate (Tropix) and luciferase activity was measured using the luciferase assay system from Promega. Measurements were made for 5 seconds on a LB 9501 Lumat luminometer (EG & G Berthold) and activity was reported as relative light units based on the ratio of luciferase to alkaline phosphatase activity. All transfections were performed in duplicate.

Results:

The ability of GATA-6 to transactivate the p21 promoter was analyzed by transient transfection assays. Two p21 promoter constructs were analyzed, the 3.8 kbp construct that contains a consensus GATA site and the 3.2 kbp construct that lacks the GATA DNA binding site. Since these p21-promoter constructs also contain functional p53 DNA binding sites (El-Deiry et al., *Cell*, 75:817–825 (1993)), p53–/– MEFs were utilized for these assays. Cultures were transfected with either wild-type GATA-6 or ΔZF-GATA-6 expression plasmids and either of the p21 promoter-luciferase construcs. Wild-type GATA-6 transactivated the 3.8 kbp p21 fragment 3.7-fold. However the 3.2 kbp promoter fragment, lacking the consensus GATA site, was not transactivated by GATA-6. Transfection of the ΔZF-GATA-6 expression plasmid which lacks the zinc finger domains necessary for DNA binding did not transactivate of either p21 -promoter constructs.

Example 10 p21-deficient cells are refractory to GATA-6-induced cell cycle arrest

To determine the functional significance of the p21 induction in GATA-6 expressing cells, p21-deficient MEFs were tested for their sensitivity to GATA-6-induced cell cycle inhibition. In contrast to the p53–/– MEFs analyzed in the previous set of experiments, many of the GATA-6 expressing p21–/– MEFs were also positive for BrdU incorporation. Quantitative analyses revealed a 37% inhibition of cell cycle activity by GATA-6 in the p21–/– MEFs, far less than the 95% inhibition seen with the isogenic p53-deficient cells.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

The SEQUENCE LISTING is presented below and is followed by what is claimed:

I claim:

1. A method for treating a subject diagnosed as having a condition associated with excessive vascular smooth muscle cell proliferation, comprising:
administering to the subject at a site where there is excessive vascular smooth muscle cell proliferation, an isolated human GATA-6 nucleic acid, in an amount effective to prevent or reduce excessive vascular smooth muscle cell proliferation at the site in vivo.

2. The method of claim 1, further comprising administering the isolated human GATA-6 nucleic acid in conjunction with a method for treating an arteriosclerotic condition.

3. The method of claim 2, wherein the method for treating an arteriosclerotic condition is a surgical method.

4. The method of claim 2, wherein the method for treating an arteriosclerotic condition is a drug therapy.

5. The method of claim 4, wherein the drug therapy includes the step of administering to the subject a cytostatic molecule in an amount effective to inhibit at least one of vascular smooth muscle cell growth and proliferation.

6. The method of claim 4, wherein the drug therapy includes the step of administering to the subject a cytokine in an amount effective to promote endothelial cell proliferation.

7. The method of claim 5, wherein the cytostatic molecule is a GAX nucleic acid.

8. The method of claim 6, wherein the cytokine is selected from the group consisting of vascular endothelial growth factor, basic fibroblast growth factor, and acidic fibroblast growth factor.

9. The method of any one of claims 1–8, wherein the isolated GATA-6 nucleic acid has a sequence comprising nucleotides 348–1697 of SEQ ID NO. 1.

10. The method of claim 9, wherein the GATA-6 nucleic acid is operably linked to a gene expression sequence.

11. The method of claim 9, wherein the GATA-6 nucleic acid is contained in or associated with a vector.

12. The method of claim 11, wherein the vector is selected from the group consisting of a biological vector and a chemical/physical vector.

13. A method for inhibiting vascular smooth muscle cell proliferation comprising:

contacting an isolated GATA-6 nucleic acid with a vascular smooth muscle cell under conditions to permit entry of the GATA-6 nucleic acid into the vascular smooth muscle cell wherein the GATA-6 nucleic acid is present in an amount effective to prevent or reduce excessive vascular smooth muscle cell proliferation.

14. The method of claim 13, wherein the isolated GATA-6 nucleic acid has a sequence comprising nucleotides 348–1697 of SEQ ID NO: 1.

15. The method of claim 14, wherein the GATA-6 nucleic acid is contained in or is associated with a vector.

16. The method of claim 15, wherein the vector is selected from the group consisting of a biological vector and a chemical/physical vector.

17. A composition comprising:

an isolated human GATA-6 nucleic acid operably linked to a gene expression sequence, wherein the gene expression sequence permits expression of the human GATA-6 nucleic acid in a human vascular smooth muscle cell; and a vector associated with the human GATA-6 nucleic acid.

18. The composition as in claim 17, wherein the composition is attached to a balloon angioplasty catheter.

19. The composition as in claim 17, further comprising:

a pharmaceutically acceptable carrier.

20. A composition as in claim 17, further comprising:

a cytostatic agent that is a nucleic acid coding for a cytostatic protein, wherein the nucleic acid coding for a cytostatic protein is operably linked to a second gene expression sequence to permit expression of the nucleic acid coding for a cytostatic protein in the human vascular smooth muscle cell.

21. The composition of claim 20 wherein, the nucleic acid coding for a cytostatic protein is a GAX nucleic acid.

* * * * *